(12) United States Patent
Mavromara et al.

(10) Patent No.: US 7,838,002 B2
(45) Date of Patent: Nov. 23, 2010

(54) HCV CORE+1 PROTEIN, METHODS FOR DIAGNOSIS OF HCV INFECTIONS, PROPHYLAXIS, AND FOR SCREENING OF ANTI-HCV AGENTS

(75) Inventors: Penelope Mavromara, Athens (GR); Niki Vassilaki, Athens (GR)

(73) Assignees: Institut Pasteur, Paris (FR); Institut Pasteur Hellenique, Athens (GR)

( * ) Notice: Subject to any disclaimer, the term of this patent is extended or adjusted under 35 U.S.C. 154(b) by 919 days.

(21) Appl. No.: 11/322,374

(22) Filed: Jan. 3, 2006

(65) Prior Publication Data
US 2006/0194281 A1    Aug. 31, 2006

Related U.S. Application Data

(63) Continuation of application No. PCT/EP2004/007996, filed on Jul. 2, 2004.

(30) Foreign Application Priority Data

Jul. 4, 2003    (EP)    ................... 03291676

(51) Int. Cl.
*A61K 39/00*    (2006.01)
*G01N 33/53*    (2006.01)

(52) U.S. Cl. .................. 424/189.1; 424/185.1; 435/7.1; 436/820

(58) Field of Classification Search .................. None
See application file for complete search history.

(56) References Cited

U.S. PATENT DOCUMENTS

2002/0076415 A1*  6/2002  Ou et al. .................. 424/189.1
2005/0202036 A1*  9/2005  Branch et al. ............. 424/189.1

FOREIGN PATENT DOCUMENTS

WO    WO 99/63941    12/1999

OTHER PUBLICATIONS

Reynolds et al (1995) EMBO Journal. 14(23): 6010-6020.*
Varaklioti, et al., "Alternate Translation Occurs Within the Core Coding Region of the Hepatitis C Viral Genome", Journal of Biological Chemistry, vol. 277, No. 20, XP002274109, ISSN: 0021-9258, pp. 17713-17721, (May 17, 2002).
Xu, et al., "Synthesis of a Novel Hepatitis C Virus Protein by Ribosomal Frameshift", EMBO Journal, Oxford University Press, Surrey, GB, vol. 20, No. 14, XP002246932, ISSN: 0261-4189, pp. 3840-3848, (Apr. 2001).
Walewski, et al., "Evidence for a New Hepatitis C Virus Antigen Encoded in an Overlapping Reading Frame", RNA New York, vol. 7, No. 5, XP002274110, ISSN: 1355-8382, pp. 710-721, (May 2001).
Vassilaki, et al., "Two Alternative Translation Mechanisms Are Responsible for the Expression of the HCV ARFP/F/Core+1 Coding Open Reading Frame", Journal of Biological Chemistry, vol. 278, No. 42, XP002274111, ISSN: 0021-9258, pp. 40503-40513, (Oct. 17, 2003).

* cited by examiner

*Primary Examiner*—Zachariah Lucas
*Assistant Examiner*—Michelle Horning
(74) *Attorney, Agent, or Firm*—Finnegan, Henderson, Farabow, Garrett & Dunner LLP

(57) ABSTRACT

The present invention relates to a novel form of core+1 protein of Hepatitis C virus (HCV), designated shorter form core+1 protein. The shorter form core+1 protein of Hepatitis C virus is the product of translation of a coding sequence consisting of all or part of a nucleotide sequence extending from nucleotide 598 to nucleotide 920 within the core+1 ORF of HCV represented on FIG. 3B. The invention also provides methods for detecting infection by Hepatitis C virus in biological samples, methods of screening compounds which interact with viral propagation in HCV infected cells or screening of compounds impaction on the expression of shorter form core+1 protein and uses of these compounds for the preparation of compositions useful for their anti-viral activities.

6 Claims, 15 Drawing Sheets

Figures 2C, 2D:
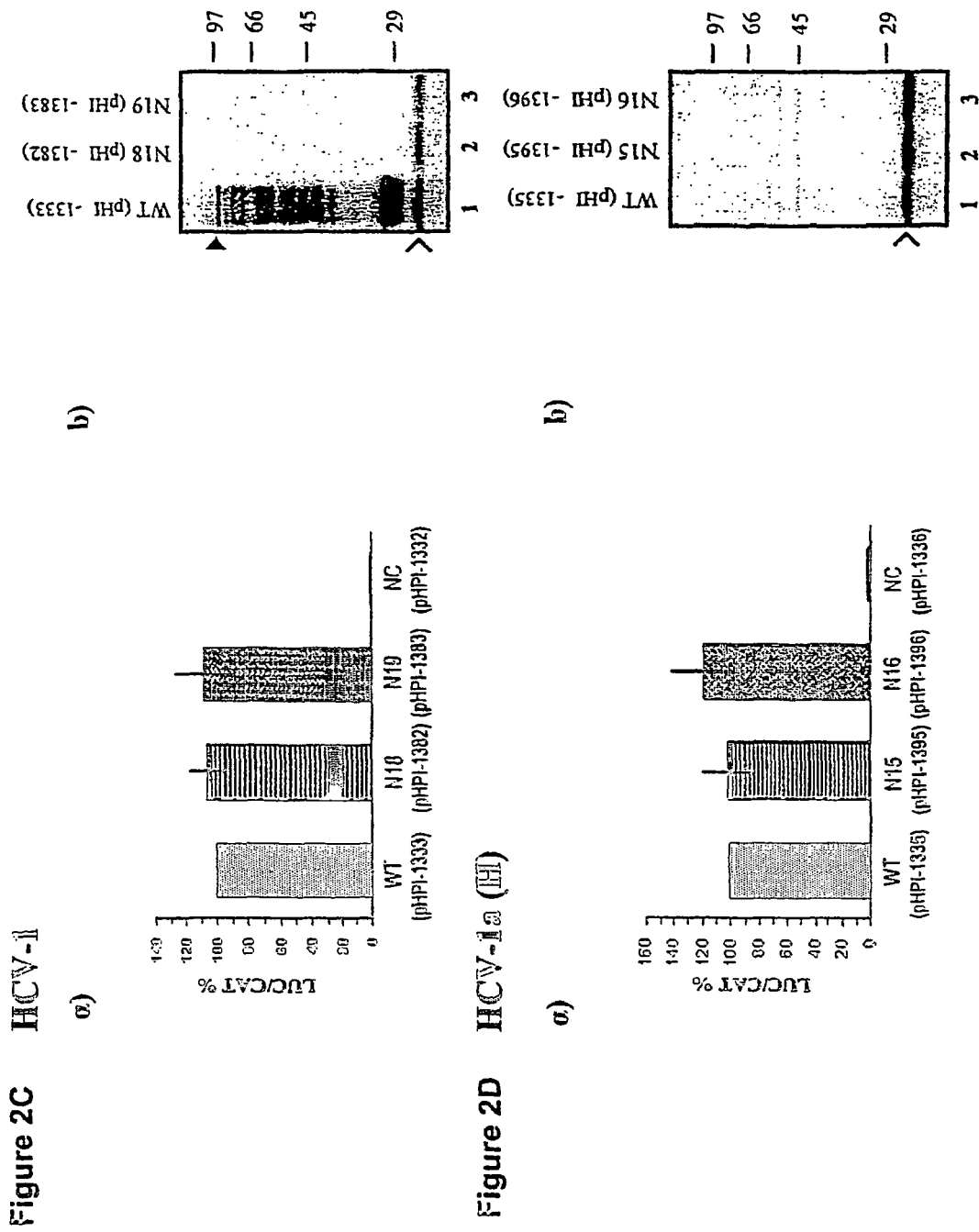

FIGURE 1
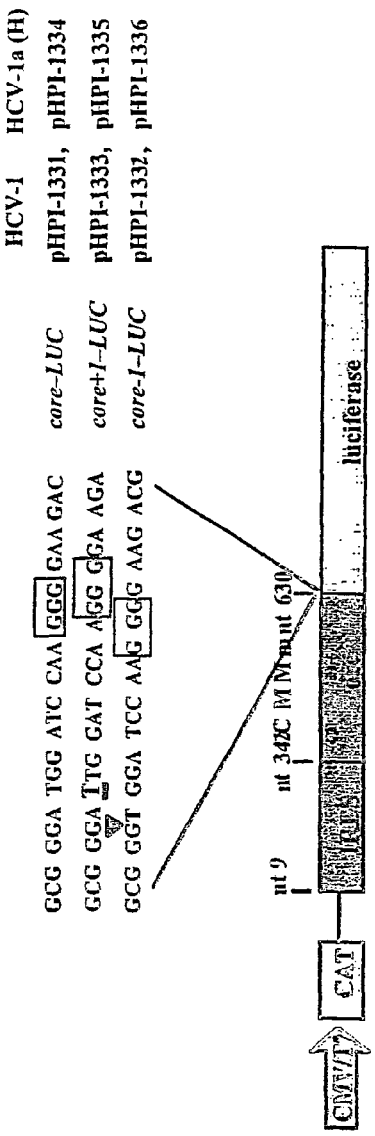
Figure 1A
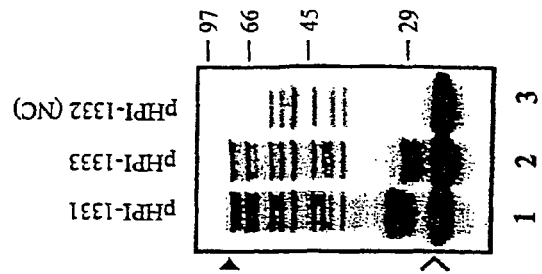
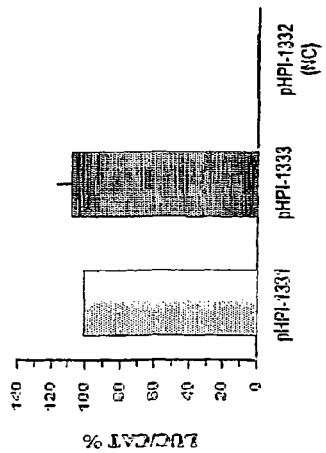
Figure 1B HCV-1

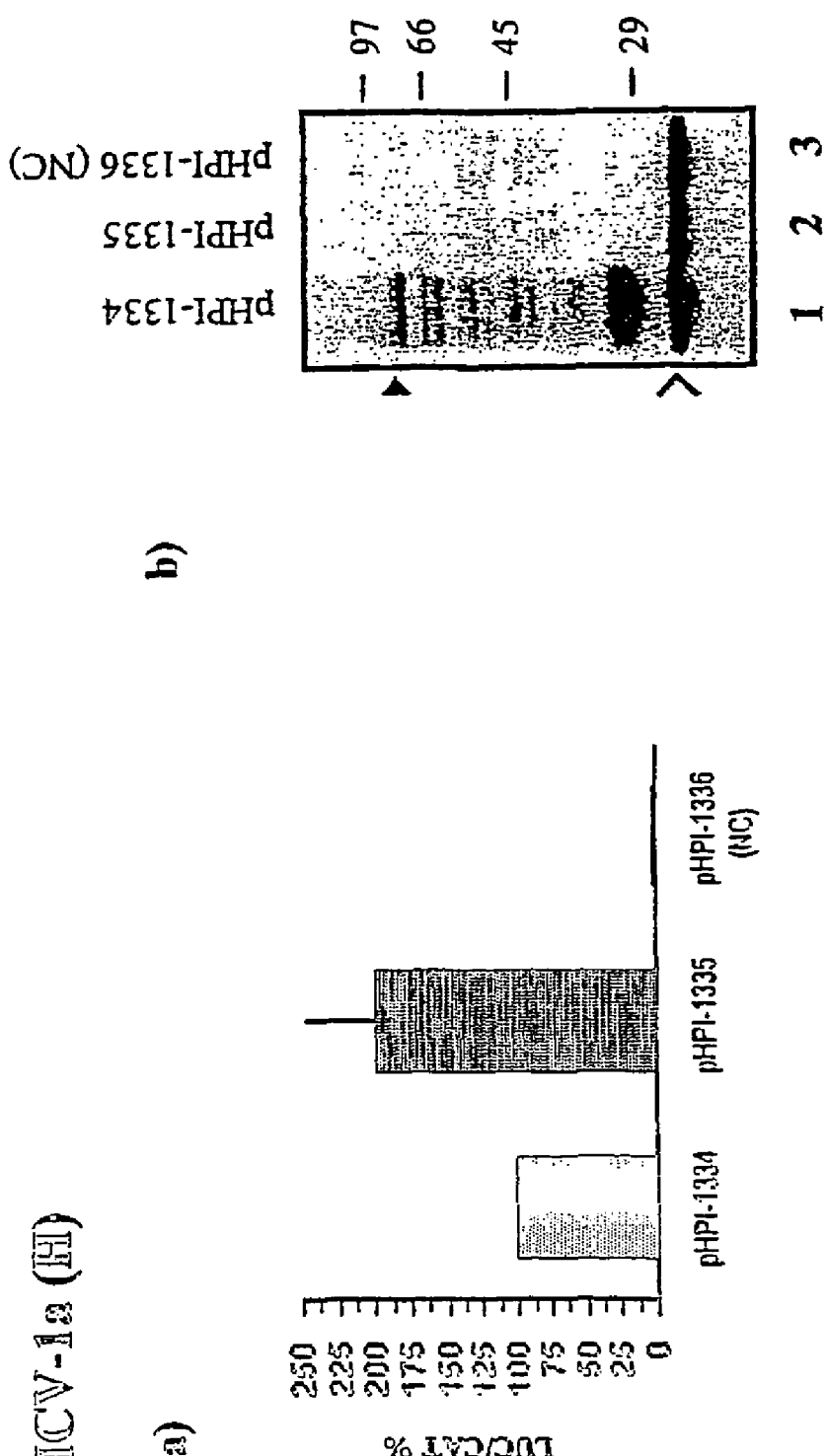
Figure 1C HCV-1a (H)

Figure 2A

```
         342                                                                                              390
          |                                                                                                |
HCV-1    ATGAGCACG AATCCTAAAC CTCAAAAAAA AAACAAACGT AACACCAACC
          M  S  T   N  P  K     P  Q  K  K   N  K  R    N  T  N

GG                  C
                                    ↑↑                  ↑
         342                        ↓↓                  ↓                                                 390
          |                                                                                                |
M18      ATGAGCACG AATCCTAAAC CTCAAAAAAA AAACAAACGT AACACCAACC
          M  S  T   N  P  K     P  Q  K  K   N  K  R    N  T  N
                                   →G (9)                →T (11)
         342                        G C                  C                                                390
          |                         ↑ ↑                  ↑                                                 |
M19      ATGAGCACG AATCCTAAAC CTCAAAAAAA AAACAAACGT AACACCAACC
          M  S  T   N  P  K     P  Q  K  K   N  K  R    N  T  N
                                 R (9) Q(10)                T (11)
```

Figure 2B

```
         342                                                                                              390
          |                                                                                                |
HCV-1a (H) ATGAGCACG AATCCTAAAC CTCAAAGAAA AACCAAACGT AACACCAACC
            M  S  T   N  P  K     P  Q  R  K   T  K  R    N  T  N

G
                                        ↑
         342                            ↓                                                                 390
          |                                                                                                |
M15      ATGAGCACG AATCCTAAAC CTCAAAGAAA AACCAAACGT AACACCAACC
          M  S  T   N  P  K     P  Q  R  K   T  K  R    N  T  N
                                      G (9) C
                                        ↑
         342                            ↓                                                                 390
          |                                                                                                |
M16      ATGAGCACG AATCCTAAAC CTCAAAGAAA AACCAAACGT AACACCAACC
          M  S  T   N  P  K     P  Q  R  K   T  K  R    N  T  N
                                         Q(10)
```

Figure 3A  Mutations in core protein coding sequence (0 frame) of HCV-1

N3: AT₃₄₂ → TA

```
          TA
          ↑        350                                            400
                    |                                               |
         ATGAGCACG AATCCTAAAC CTCAAAAAAA AAACAAACGT AACACCAACC GTCGCCCACA
          M  S  T   N  P  K    L  K  K   N  K  R    N  T  N     V  A  H

TAA
                                ↑
          401
           |
         GGACGTCAAG TTCCCGGGTG GCGGTCAGAT CGTTGGTGGA GTTTACTTGT ..........
          D  V  K    F  P  G    G  G  Q   I  V  G  G   V  Y  L

N6: CCG₄₁₀ → TAA 920
          881                                                      |
           |
         CCTGCTCTCT TGCTTGACTG TGCCCGCCTC GGCCTACCAA
          L  L  S    C  L  T    V  P  A  S   G  L  P  T
```

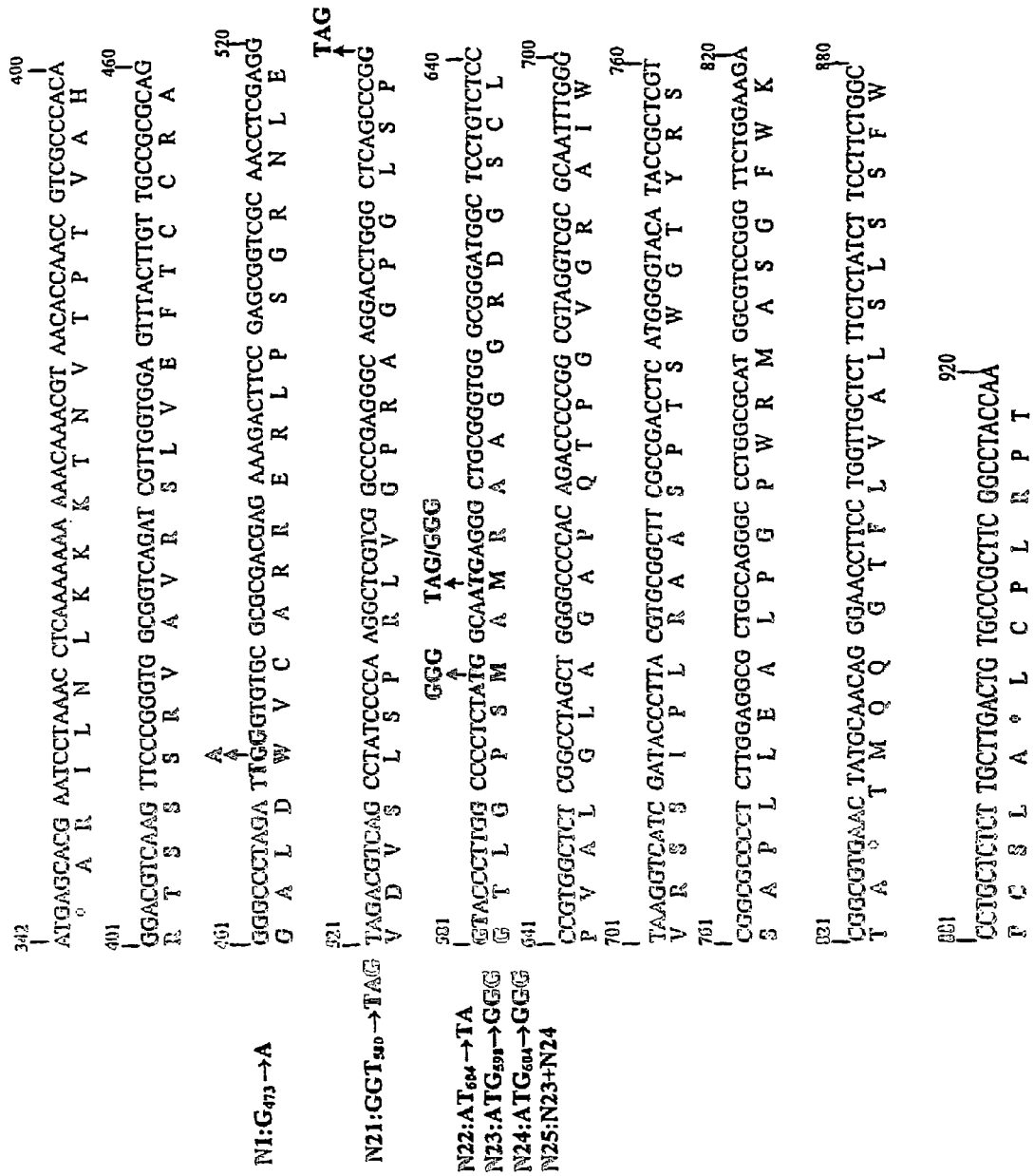

Figure 3B ARFP/F/core+1 coding sequence (+1 frame) of HCV-1 and mutations in core+1 coding sequence

```
342                                                          400
ATGAGCACG AATCCTAAAC CTCAAAAAAA AAACAAACGT AACACCAACC GTCGCCCACA
  °  A  R   I  L  N   L  K  K  K  T  N  V   T  P  T   V  A  H 401                                                          460
GGACGTCAAG TTCCCGGGTG GCGGTCAGAT CGTTGGTGGA GTTTACTTGT TGCCGCGCAG
R  T  S  S  S  R  V  A  V  R  S  L  V  E  F  T  C  C  R  A

A
N1:G473→A        ↑
461                                                          520
GGGCCCTAGA TTGGGTGTGC GCGCGACGAG AAAGACTTCC GAGCGGTCGC AACCTCGAGG
G  A  L  D  W  V  C  A  R  R  E  R  L  P  S  G  R  N  L  E

TAG
N21:GGT580→TAG                                                 ↑
521
TAGACGTCAG CCTATCCCCA AGGCTCGTCG GCCCGAGGGC AGGACCTGGG CTCAGCCCGG
V  D  V  S  L  S  P  R  L  V  G  P  R  A  G  P  G  L  S  P

GGG      TAG/GGG
N22:AT604→TA      ↑          ↑
N23:ATG598→GGG
N24:ATG604→GGG
N25:N23+N24
581                                                          640
GTACCCTTGG CCCCTCTATG GCAATGAGGG CTGCGGGTGG GCGGGATGGC TCCTGTCTCC
G  T  L  G  P  S  M  A  M  R  A  A  G  G  R  D  G  S  C  L 641                                                          700
CCGTGGCTCT CGGCCTAGCT GGGGCCCCAC AGACCCCCGG CGTAGGTCGC GCAATTTGGG
P  V  A  L  G  L  A  G  A  P  Q  T  P  G  V  G  R  A  I  W 701                                                          760
TAAGGTCATC GATACCCTTA CGTGCGGCTT CGCCGACCTC ATGGGGTACA TACCGCTCGT
V  R  S  S  I  P  L  R  A  A  S  P  T  S  W  G  T  Y  R  S 761                                                          820
CGGCGCCCCT CTTGGAGGCG CTGCCAGGGC CCTGGCGCAT GGCGTCCGGG TTCTGGAAGA
S  A  P  L  L  E  A  L  P  G  P  W  R  M  A  S  G  F  W  K 821                                                          880
CGGCGTGAAC TATGCAACAG GGAACCTTCC TGGTTGCTCT TTCTCTATCT TCCTTCTGGC
T  A  °  T  M  Q  Q  G  T  F  L  V  A  L  S  L  S  S  F  W 881                                  920
CCTGCTCTCT TGCTTGACTG TGCCCGCTTC GGCCTACCAA
P  C  S  L  A  °  L  C  P  L  R  P  T
```

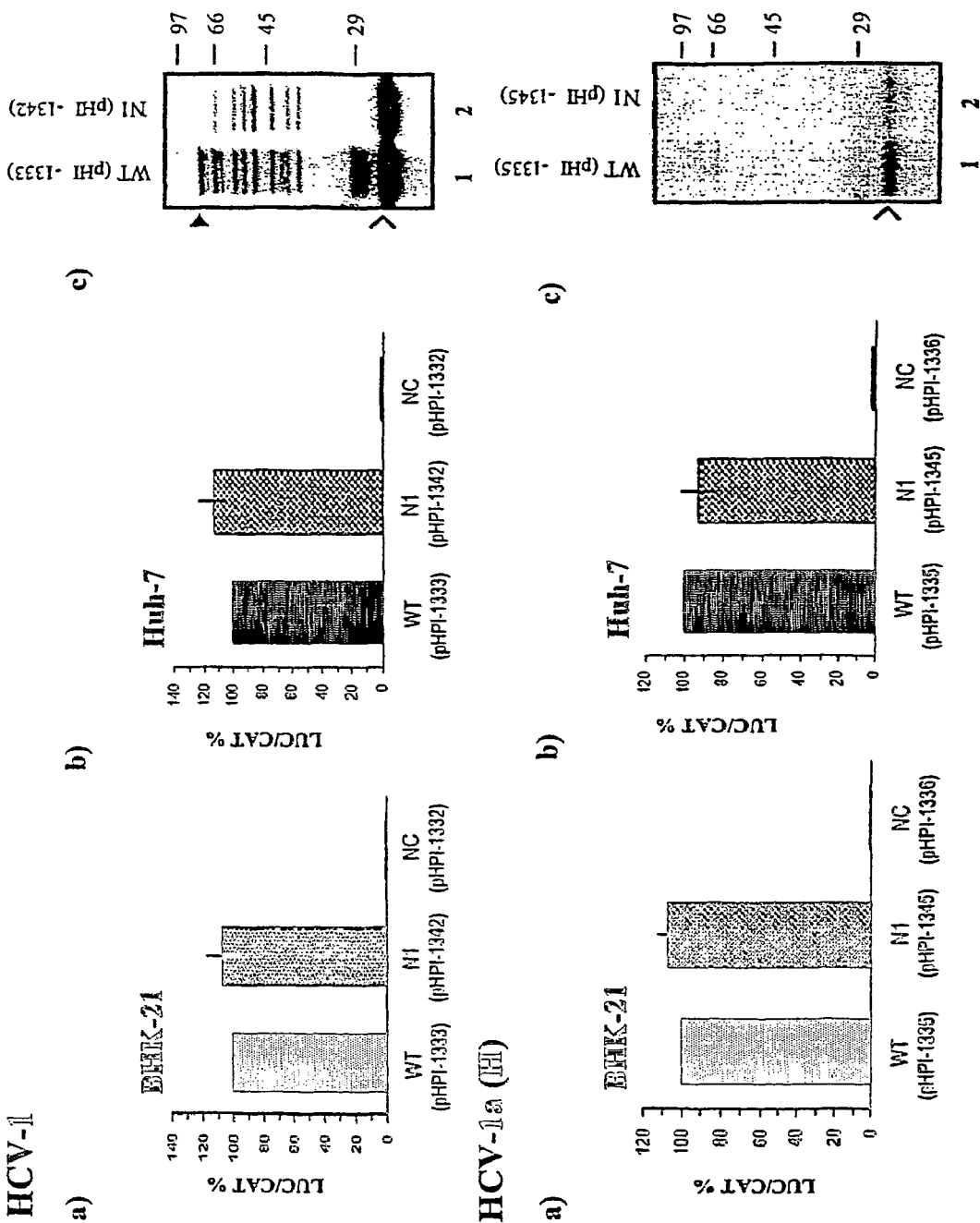
Figure 5A HCV-1
Figure 5B HCV-1a (H)

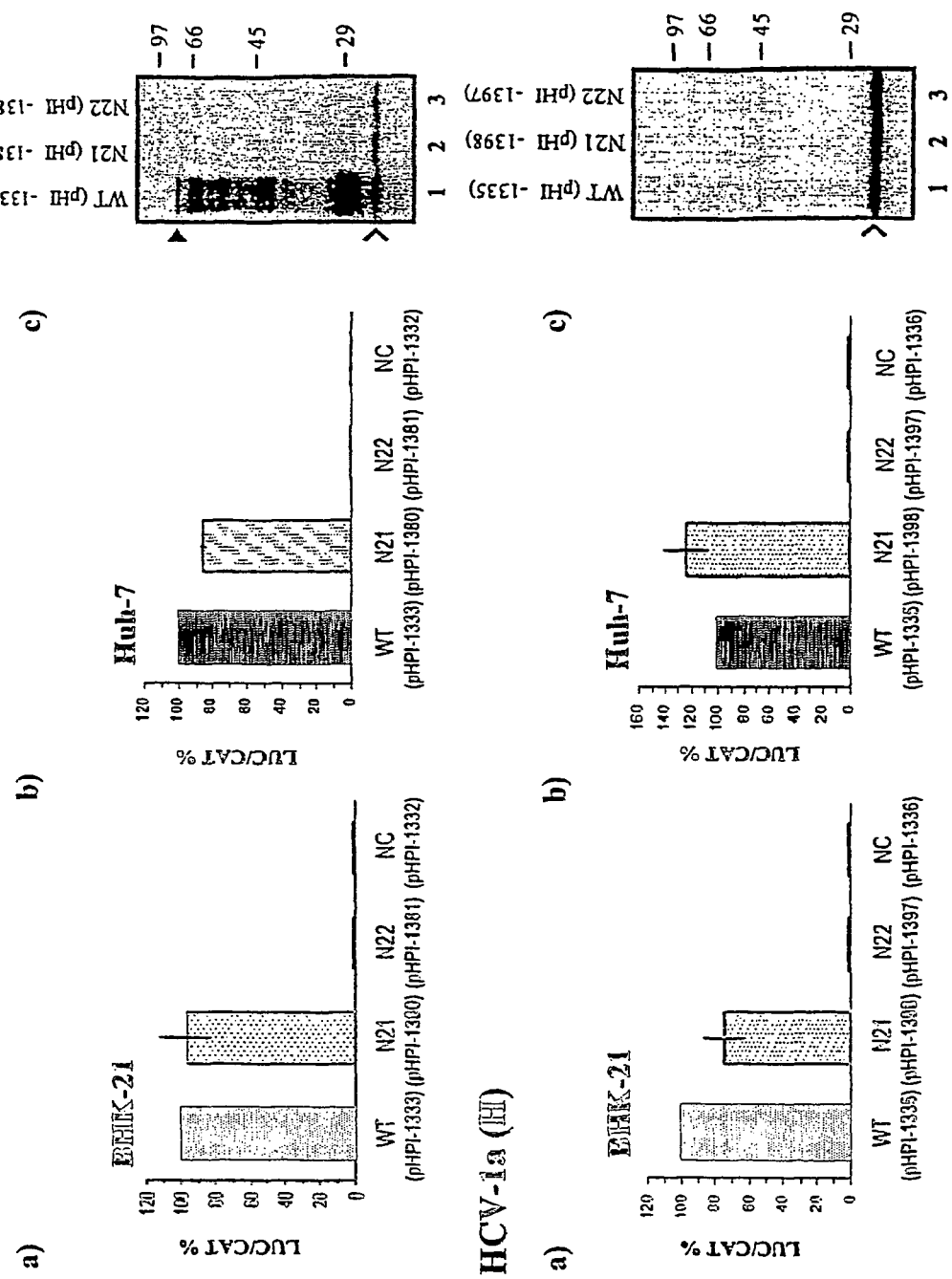
Figure 5C HCV-1
Figure 5D HCV-1a (H)

FIGURE 6
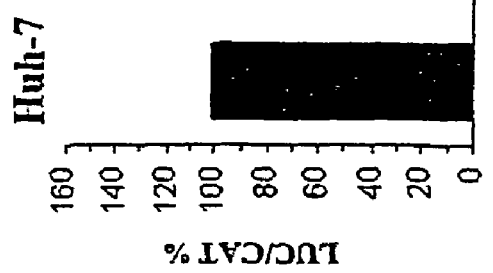
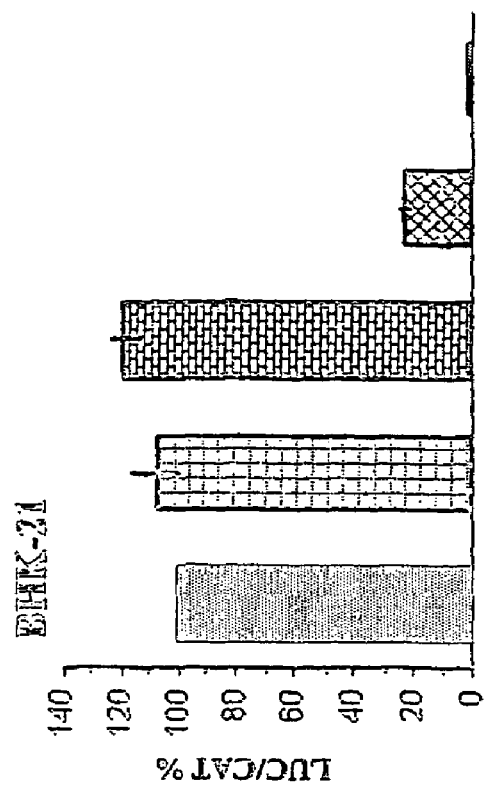

Figure 8A

Figure 9B

```
af011752.type1a  SSIPLRAASPTSWGTYRSSAPLLEALPGPWRMASGEWKTA
ab086050.type1b  SSIPSHAASPTSWGTYRSSAPLLEALPGPWRMASGEWKTG
af177036.type2a  SSIP------------------------------------
ab030907.type2b  SSTPSRVVLPISWGTSLSLAPLSEASPELWHTVLGSWKTG
u10211.type2c    SSIP------------------------------------
d49746.type2e    SSIPSPAALPTSWGTSPSSAPLLGALPEPSRMA-------
d49757.type2f    SSTPSRVALPTSWGTFPSSAPRLVALPELSHMV-------
ab031663.type2k  SSIPLRVVLPISWGTYPSSAPLAALPEHSRMA--------
af046966.type3a  SSIPLRVDSPTSWGTSRSSAPPWEASQEPSRMA-------
u10236.type4a    SSIP------------------------------------
L38330.type4c    SSIP------------------------------------
u10192.type4d    SSIP------------------------------------
u10237.type4e    SSIP------------------------------------
L38332.type4f    SSIPSRAASPTSWGTSRS----------------------
u10210.type5b    SSIP------------------------------------
L38339.type6a    SSIP------------------------------------
d84263.type6d    SSIPLPAALPTSWGTSLSSVPP------------------
d49740.type6e    SSIPLLAASPTSWGTSPS----------------------
zd84265.type6h   SSIPSMA---------------------------------
yd84264.type6k   SSIP------------------------------------
```

List of oligonucleotides and constructs used in the mutational analysis

| Mutation | Oligonucleotides (sense) | In vitro plasmids | In vivo plasmids |
|---|---|---|---|

WT: pHPI-1333 / HCV-1 / CAT-IRES-core-LUC

| Mutations | | | |
|---|---|---|---|
| N1 | 5'-280 CAGGGGCCCCTAGATTAGGTGTGCGCGCGAC -3' | pHPI-1342 | pHPI-1342 |
| N3 | 5'-334 CGTGCACCTAGAGCACGGATCCTAAACCTC -3' | pHPI-1343 | pHPI-1343 |
| N6 | 5'-401 CGTCAAGTTCTAAGGTGCGGTC -3' | pHPI-1344 | pHPI-1344 |
| N18 | 5'-350 CCTAAACCTCAAGGAAAACCAAACCAAACGTAACACC -3' | pHPI-1382 | pHPI-1382 |
| N19 | 5'-350 CCTAAACCTCAAAAGACAAACCAAACGTAACACC -3' | pHPI-1383 | pHPI-1383 |
| N21 | 5'-571 CTCAGCCCGTAGACCCTTGGCC -3' | pHPI-1380 | pHPI-1380 |
| N22 | 5'-585 CTCTATGGCATAGAGGGCTGCGGGT -3' | pHPI-1381 | pHPI-1381 |
| N23 | 5'-507 TTGGCCCCTCTGGGCAGGGAGGGCTGCGGGT -3' | pHPI-1399 | pHPI-1399 |
| N24 | 5'-507 CTCTATGGCAGGGAGGGCTGCGGGT -3' | pHPI-1400 | pHPI-1400 |
| N25 | 5'-507 TTGGCCCCTCTGGGCCAGGGAGGGCTGCGGGT -3' | pHPI-1401 | pHPI-1401 |

NC: pHPI-1332
WT: pHPI-1335 / HCV-1a (H) / CAT-IRES-core-LUC

| Mutations | | | |
|---|---|---|---|
| N1 | 5'-280 CAGGGGCCCCTAGATTAGGTGTGCGCGCGAC -3' | pHPI-1345 | pHPI-1345 |
| N3 | 5'-334 CGTGCACCTAGAGCACGGATCCTAAACCTC -3' | pHPI-1346 | pHPI-1346 |
| N6 | 5'-401 CGTCAAGTTCTAAGGTGCGGTC -3' | pHPI-1347 | pHPI-1347 |
| N15 | 5'-350 CCTAAACCTCAAGGAAAACCAAACCAAACGTAACACC -3' | pHPI-1395 | pHPI-1395 |
| N16 | 5'-350 CCTAAACCTCAAAGACAAACCAAACGTAACACC -3' | pHPI-1396 | pHPI-1396 |
| N21 | 5'-571 CTCAGCCCGTAGACCCTTGGCC -3' | pHPI-1398 | pHPI-1398 |
| N22 | 5'-590 CTCTATGGCATAGAGGGTTGCGGGT -3' | pHPI-1397 | pHPI-1397 |

NC: pHPI-1336

FIGURE 9

HCV CORE+1 PROTEIN, METHODS FOR DIAGNOSIS OF HCV INFECTIONS, PROPHYLAXIS, AND FOR SCREENING OF ANTI-HCV AGENTS

CROSS REFERENCE TO RELATED APPLICATIONS

This application is a Continuation of PCT International Application No. PCT/EP2004/007996, filed on Jul. 2, 2004, which claimed the priority of European Patent Application No. 03291676.9, filed Jul. 4, 2003, the contents of both of which are incorporated herein by reference.

The present invention relates to a novel form of core+1 protein of Hepatitis C virus (HCV), designated shorter form core+1 protein. The invention also provides methods for detecting infection by Hepatitis C virus in biological samples, methods of screening compounds which interact with viral propagation in HCV infected cells and advantageously decrease inhibit or prevent viral propagation or screening of compounds impaction on the expression of shorter form core+1 protein and uses of these compounds for the preparation of compositions useful for their anti-viral activities. The invention also proposes to use the shorter form core+1 protein of the invention to derive immunogenic compositions for protection against HCV infection or against its consequences.

Hepatitis C is a viral infection of the liver which has also been referred to as "non A, non B hepatitis" (NANBH) until identification of the causative agent. Hepatitis C virus is one of the viruses (A, B, C, D and E), which together account for the majority of cases of viral hepatitis. Hepatitis C virus was first identified in 1989 (Choo et al. 1989) and defined as a common cause of liver disease with an estimated 170-million infected people worldwide. Hepatitis C virus (HCV) infection affects the liver, which causes hepatitis, i.e., an inflammation of the liver. 75 to 85% of persons infected with HCV progress to chronic infection, approximately 20% of these cases develop complications of chronic hepatitis C, including cirrhosis of the liver or hepatocellular carcinoma after 20 years of infection (Di Bisceglie 2000). The current recommended treatment for HCV infections is a combination of interferon and ribavirin drugs, however the treatment is not effective in all cases and the liver transplantation is indicated in hepatitis C-related end-stage liver disease. At present, there is no vaccine available to prevent HCV infection, therefore all precautions to avoid infection must be taken.

HCV is a (+) sense single-stranded enveloped RNA virus in the Hepacivirus genus within the Flaviviridae family. The viral genome is approximately 10 kb in length and encodes a 3011 amino acid polyprotein precursor. The HCV genome has a large single open reading frame (ORF) coding for a unique polyprotein, said polyprotein being co- and post-translationally processed by cellular and viral proteases into three structural protein, i.e., core, E1 and E2 and at least six non-structural NS2, NS3, NS4A, NS4B, NS5A and NS5B proteins (Houghton 1996 and Reed et al. 2000).

Initiation of translation of the HCV genome is controlled by an internal ribosome entry site (IRES) located mainly within the 5'-non coding region of the viral RNA, between nucleotides 42 and 341 or 356, the 3' limit being controversial. The core protein, which forms the viral nucleocapsid, is predicted to be 191 amino acids in length and to have a molecular mass of 23 kDa (p23). Further processing of p23 produces the mature core protein (p21), consisting of between 173-182 amino acids. It has been previously reported that a protein having a molecular weight of about 17 kDa is also expressed from the core protein-coding sequence of some HCV isolates both in vitro and in vivo, e.g. in E. coli cells. This additional HCV polypeptide of 16/17 kDa (p16/p17), consisting of maximum 160 amino acids, is encoded by the open reading frame that overlaps the core gene in the +1 frame (core+1 ORF) and is syntheTized in vitro as a result of a +1 ribosomal frameshift for translation.

This 16/17 kDa polypeptide is named ARFP for Alternative Reading Frame Protein or F for Frameshift protein or core+1 according to the location of this novel protein. The ARFP/F/core+1 protein is synthetized in vitro from the initiator codon of the polyprotein sequence followed by a +1 ribosomal frameshift operating in the region of core codons 8-14 (Xu et al. 2001, Varaklioti et al. 2002).

More recently, the expression of the core+1 protein coding sequence has been assayed in mammalian cells, i.e. in vivo, in order to investigate the biological importance of the core+1 protein. It has been shown that expression of the core+1 ORF of HCV-1 and of HCV-1a (H) in rabbit reticulocyte lysates (in vitro) can be obtained respectively for HCV-1 isolate whereas it is not detected for HCV-1a(H) isolate (Varaklioti et al. 2002). Indeed, the core+1 protein has been synthesized in vitro when expressing core+1 ORF from HCV-1 but has not been detected when expressing core+1 ORF from HCV-1a (H). It is reminded that HCV-1 and HCV-1a(H) isolates of HCV, although belonging to the same genotype, have different sequences at the frameshift site located in codons 8-14 of HCV-1. The difference especially consists in the lack of the 10-A nucleotide residues in the HCV-1a(H) sequence at the putative frameshift site. In order to provide some data on expression mechanisms of core+1 protein the inventors have studied said expression in vivo.

The results disclosed in the present invention indicate that, unlike to the in vitro expression studies, both HCV-1 and HCV-1a (H) core coding sequences efficiently allow expression of the core+1 ORF in transfected mammalian cells. The transfection and expression experiments carried out in mammalian cells have also enabled the present inventors to identify that in vivo expression of core+1 ORF is associated with synthesis of a new protein which expression follows a new alternative translation initiation mechanism of core+1 ORF when compared to the mechanism identified for the in vitro expression of core+1 protein. Said alternative mechanism directs the synthesis of a shorter form of core+1 protein, in vivo.

Particular species of HCV-1 and HCV-1a (H) have been disclosed, respectively, in Genebank under references No. M62321 and No. M67463.

Viruses, which are subject to genome size constraints have developed different strategies to expand their coding capacity, such as ribosomal frameshifting or internal translational initiation. The ribosomal frameshifting consists in avoiding a termination codon, which would otherwise have been encountered by the ribosome, and instead creates a protein with extra amino acid sequences at its C terminal end. Therefore, in ribosomal frameshifting a directed change of translational reading frame allows the synthesis of a single protein from two or more overlapping genes. The internal translational initiation consists in escaping from an upstream initiator codon according to different mechanisms including leaky-scanning and ribosome shunting and internal ribosome entry site. Such a mechanism is apparently used for in vivo expression of shorter form core+1 protein.

The invention thus provides a new protein of HCV life cycle, which is designated shorter form core+1 protein and which can be obtained by in vivo expression of the core+1 coding sequence or ORF, especially in mammalian cells.

The invention also relates to nucleic acid sequences encoding said shorter form core+1 protein.

The invention also provides methods for detecting in a biological sample of an individual the presence or absence of the shorter form core+1 protein giving evidence of Hepatitis C virus infection.

The invention also provides use of the shorter form core+1 protein of the invention in an immunogenic composition. An immunogenic composition of the invention may advantageously be prepared in order to elicit a CTL response against HCV infection, in a patient.

The shorter form core+1 HCV protein may also be involved in the preparation of therapeutic composition aiming at interacting with the consequences of HCV infection, especially when persistent infection appears.

The invention also provides means for screening compounds, especially compounds having antiviral activity, as a result of interaction with in vivo expression of the core+1 ORF directing translation of shorter form core+1 protein. Among the several advantages of the present methods, it should be noted that these screening methods are appropriate for routine high throughput screening of compounds capable of interacting with viral propagation and control of life cycle of the virus especially capable of inhibiting or preventing viral propagation.

Moreover, the invention also provides for the use of the compounds capable of interacting with viral propagation and control of life cycle of the virus, especially compounds capable of inhibiting or preventing viral propagation, advantageously as a result of their capacity to interact with expression of shorter form core+1 protein in HCV infected cells, which compounds would be useful for the preparation of a drug for the treatment of disorders induced by or associated with infection of Hepatitis C virus.

A first object of the invention is thus a shorter form core+1 protein of HCV which is the product of translation of a coding sequence consisting of all or part of nucleotide sequence extending from nucleotide 598 to nucleotide 920 within the core+1 ORF of HCV represented on FIG. 3B.

In a particular embodiment, the shorter form core+1 protein is encoded by a nucleotide sequence having a translation initiation codon (ATG) at position 598 or by a nucleotide sequence having an ATG at position 604 of the HCV core+1 coding sequence.

In a particular embodiment, the shorter form core+1 protein is encoded by:

(i) a nucleotide sequence extending from nucleotide 598 to nucleotide 828 of the sequence represented on FIG. 3B; or (ii) a nucleotide sequence extending from nucleotide 598 to nucleotide 897 of the sequence represented on FIG. 3B; or (iii) a nucleotide sequence extending from nucleotide 604 to nucleotide 828 of the sequence represented on FIG. 3B; or (iv) a nucleotide sequence extending from nucleotide 604 to nucleotide 897 of the sequence represented on FIG. 3B; or (v) a nucleotide sequence extending from nucleotide 604 to nucleotide 920 of the sequence represented on FIG. 3B.

As used herein, the expression "shorter form core+1 protein", or "in vivo core+1 protein" refer to the Hepatitis C virus proteins obtainable in vivo, in cells infected with HCV, or in cells transfected with a DNA construct comprising core coding sequence or core+1 ORF. A predominant shorter form of core+1 is especially produced in vivo which is smaller than the 16/17 kDa core+1 in vitro synthesized product, as it is predicted to have a calculated molecular weight of less than 10 kDa. Furthermore, the shorter form core+1 protein does not contain the first 10 consecutive A residues of the core protein. These A residues are located codons 8-11 (nucleotides 364-373) of the HCV-1 genome and have a great importance on the expression of the core+1 ORF. This specific difference of molecular weight explains the term "shorter form core+1 protein".

As used herein, the expression "core+1 ORF" refers to the nucleotide sequence such as represented FIG. 3B of the present application which is comprised within the "core coding sequence" of HCV. Said core+1 ORF, begins at nucleotide 342 with translation initiation codon and extends up to nucleotide at position 920 (U.S. Ser. No. 09/644,987) in the sequence illustrated on FIG. 3B.

It is pointed out that shorter form core+1 protein is encoded by core+1 ORF or by core coding sequence, when said nucleotide sequences are expressed in vivo.

The invention relates further to a shorter form core+1 protein of HCV which is obtainable in vivo by expression of the core+1 open reading frame (ORF) which is contained in nucleotide sequence extending from nucleotide at position 342 to nucleotide at position 920, preferably to nucleotide at position 826 of the nucleotide sequence represented on FIG. 3B and which calculated molecular weight is less than 10 kDa.

It is emphasized that shorter form core+1 protein is obtainable in vivo independently of the expression of the HCV polyprotein and also independently of the expression of core+1 protein. Said expression in vivo uses the same frame as the one used for core+1 expression in the core+1 ORF but does not involve the frameshift transfection mechanism required for core+1 in vitro expression.

In an other embodiment, the shorter form core+1 protein is the expression product of the core+1 ORF in mammalian cells.

In a preferred embodiment, the shorter form core+1 protein is recognized by a serum of patients infected with HCV. In the same way circulating anti-core+1 antibodies have been detected in HCV-infected individuals, suggesting that this protein is produced during natural HCV infection.

In a preferred embodiment, the shorter form core+1 protein comprises the amino acid sequence extending from amino acid residue corresponding to nucleotide 598 to amino acid residue corresponding to nucleotide 828, or to nucleotide 897 or to nucleotide 920 of the sequence represented on FIG. 3B. In another preferred embodiment, the shorter form core+1 protein comprises the amino acid sequence extending from amino acid residue corresponding to nucleotide 604 to amino acid residue corresponding to nucleotide 828, or to nucleotide 897 or to nucleotide 920 of the sequence represented on FIG. 3B.

The start and/or stop codons disclosed for shorter core+1 protein may vary depending on the HCV isolate considered. The above positions of start and stop codons are given with respect to the amino-acid sequence of FIG. 3. Although shorter form core+1 protein ending with codon corresponding to nucleotide 826 can be regarded as a preferred form of said protein, the above given longer sequences may be encoded simultaneously or alternatively.

The invention further concerns peptides contained within the shorter form core+1 protein, especially peptides useful as epitopes. For the purposes of the present invention, the term "epitope," when referring to a peptide, is to be considered as an antigenic determinant or the immunologically active region of said peptide. It is the portion of said immunogenic peptide which is bound specifically by antibody or TCR. Said epitope on a peptide antigen may involve elements of the primary, secondary, tertiary, and even quaternary structure of the peptide and contains at least three residues. The present invention provides a particular peptide of interest, useful as epitope, and having the following sequence: NH$_2$-T-Y-R-S-S-A-P-L-L-E-A-L-P-G-P-COOH (SEQ ID NO:61)

Such peptide of interest comprises amino-acid sequence extending from amino-acid residue corresponding to nucleotide 748 to amino-acid residue corresponding to nucleotide 792, or to nucleotide 795 in the sequence of FIG. 3B.

Variants of this peptide, such as those obtained by deletions, additions or substitutions of amino acids in the peptide, are also encompassed by the present invention and can be obtained by methods known in the art, as long as these variants can elicit antibodies or can immunologically react with antibodies directed against the above sequence.

Examples of variants of this peptide of interest encompassed by the present invention can be illustrated as follows and according to FIG. 8 (SEQ ID NOS 2-13, respectively in order of appearance):

NH$_2$-T-X-R-S-S-A-P-L-L-E-A-L-P-G-P-COOH where X=F or S;

NH$_2$-T-Y-X-S-S-A-P-L-L-E-A-L-P-G-P-COOH where X=L, P or R;

NH$_2$-T-Y-R-S-X-A-P-L-L-E-A-L-P-G-P-COOH where X=L;

NH$_2$-T-Y-R-S-S-X-P-L-L-E-A-L-P-G-P-COOH where X=V;

NH$_2$-T-Y-R-S-S-A-P-X-L-E-A-L-P-G-P-COOH where X=P or R;

NH$_2$-T-Y-R-S-S-A-P-L-X-E-A-L-P-G-P-COOH where X=S or W;

NH$_2$-T-Y-R-S-S-A-P-L-L-X-A-L-P-G-P-COOH where X=G, V, A, or E;

NH$_2$-T-Y-R-S-S-A-P-L-L-E-A-X-P-G-P-COOH where X=S;

NH$_2$-T-Y-R-S-S-A-P-L-L-E-A-L-X-G-P-COOH where X=Q;

NH$_2$-T-Y-R-S-S-A-P-L-L-E-A-L-P-X-P-COOH where X=E;

NH$_2$-T-Y-R-S-S-A-P-L-L-E-A-L-P-G-X-COOH where X=L or H;

NH$_2$-T-Y-R-S-S-A-P-L-L-E-A-L-P-G-P-X-COOH where X=C, W or S.

Such peptides are interesting especially for the preparation of antibodies, either polyclonal or monoclonal.

The translation initiation codon of shorter form core+1 protein may vary depending on HCV isolate. Some isolates contain two ATG which both may be used for synthesis of shorter form core+1 protein. Other isolates contain only one ATG for said protein.

Figure 8A:
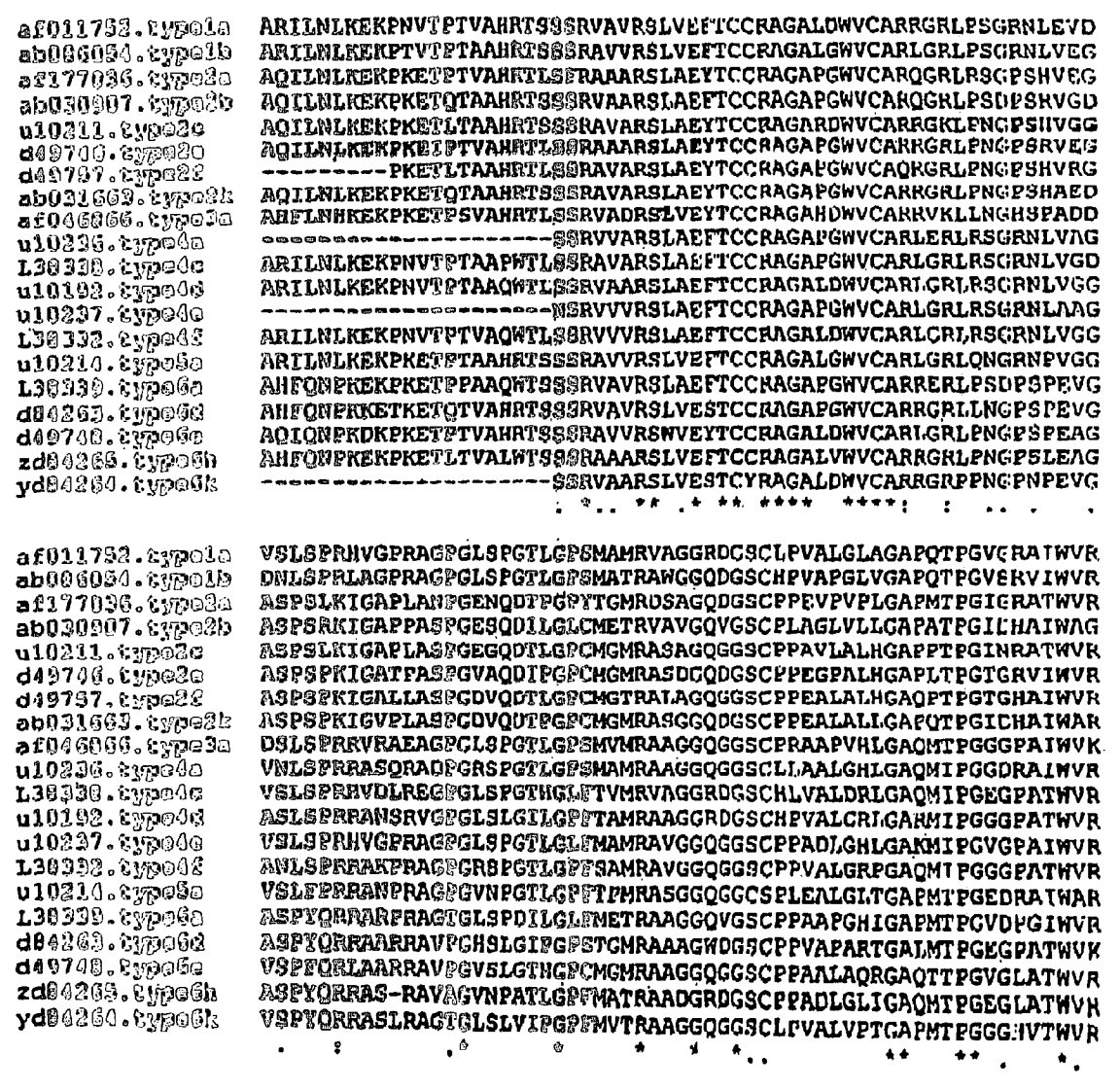

Various shorter form core+1 proteins are for example derivable from the proteins alignment of the sequence of FIG. 3B, with the amino-acid sequences disclosed in FIG. 8, which correspond to the proteins expressed by variants.

The invention also concerns a mosaic of proteins encoded by the above defined core coding sequence of HCV. Such a mosaic contains at least two proteins selected among core protein, core+1 protein, shorter form core+1 protein or their derivatives, including derivatives encoded by said sequence and involving further frameshift mechanism in the 3' terminal part of the core coding sequence.

These compositions of proteins can comprise proteins of the same isolates or from different HCV isolates.

The invention also relates to a nucleotide sequence consisting in a fragment of the nucleotide sequence extending from nucleotide 342 to nucleotide 920 represented on FIG. 3B, which fragment is capable of encoding a shorter form core+1 protein of HCV when transfected in mammalian cells under expression conditions.

More specifically, it is shown that the nucleotide sequence encoding a shorter form core+1 protein comprises a nucleotide sequence extending from nucleotide 598 or from nucleotide 604 to nucleotide 828 within the core+1 coding sequence of FIG. 3B.

In a specific embodiment, the nucleotide sequence encoding a shorter form core+1 protein is chosen among:

(i) a nucleotide sequence extending from nucleotide 604 to nucleotide 828 of the sequence represented on FIG. 3B;

(ii) a nucleotide sequence extending from nucleotide 604 to nucleotide 897 of the sequence represented on FIG. 3B;

(iii) a nucleotide sequence extending from nucleotide 604 to nucleotide 920 of the sequence represented on FIG. 3B;

(iv) a nucleotide sequence extending from nucleotide 598 to nucleotide 828 of the sequence represented on FIG. 3B;

(v) a nucleotide sequence extending from nucleotide 598 to nucleotide 897 of the sequence represented on FIG. 3B;

(vi) a nucleotide sequence extending from nucleotide 598 to nucleotide 920 of the sequence represented on FIG. 3B; and (vii) a fragment of sequence (i), (ii), (iii), (iv), (v), or (vi), which is capable of encoding a shorter form core+1 protein, as defined above, in mammalian cells or an epitope thereof.

The invention also provides variant nucleotide sequences derived from different isolates, which encode the shorter form core+1 proteins illustrated on FIG. 8.

The invention thus provides a nucleotide sequence comprising a Hepatitis C virus core protein coding sequence which is derived from the nucleotide sequence represented on FIG. 3B as a result of one or several mutation selected among the following:

in 9$^{th}$ and 11$^{th}$ codons a mutation which respectively corresponds to a triple substitution of two A to G and of an A to C; or in 9$^{th}$, 10$^{th}$ and 11$^{th}$ codons a mutation which respectively consists of a substitution of one A to G and two A to C; or in 9$^{th}$ codon a mutation which consists of a substitution of A to G or in 10$^{th}$ codon a mutation which consists of a substitution of A to C; or a substitution of an initiator codon into a terminator codon; or a substitution of the 25$^{th}$ codon into a stop codon; or a substitution of the 43$^{rd}$ codon into a stop codon; or a substitution of the 79$^{th}$ codon into a stop codon; or a substitution of the 87$^{th}$ codon into a stop codon; or a substitution of the 85$^{th}$ codon into a stop codon and/or a substitution of the 87$^{th}$ codon into a stop codon.

The nucleotide sequences of the invention are especially under a purified form, i.e., they are isolated from their natural environment in HCV.

The above mutations consist in generating a missense codon in a specific position of the nucleotide sequence, for detecting codons which are critical for core+1 expression in vivo. As referred to herein, a "stop codon", "missense codon", "nonsense codon", "terminator codon" and "chain-terminating codon" are capable of stopping the translation since any amino acids correspond to said codon. The coding sequences of stop codon are often UAA, UAG and UGA. The presence of a stop codon disrupts the core+1 coding region and fails to support the production of the core+1 protein whether said stop codon is in frame with the open reading frame (ORF) of core+1 coding region.

The invention also provides nucleotide sequences which are functional variants of said nucleotide sequences and having at least 70% identity, preferably 80% or 90% identity.

As used herein, the term "variant" refers to a nucleotide sequence substantially homologous to HCV shorter form core+1 nucleotide sequence, which has however undergone mutations, especially one or more deletions, insertions or substitutions resulting of the genetic code degeneracy. The variant nucleotide sequence is at least 70% identical to a nucleotide sequence encoding native shorter form core+1 protein, most preferably at least 80% or 90% identical. Determination of variant sequences according to the present invention may be performed using the GAP computer program (Devereux et al, Nucl. Acids Res. 12: 387, 1984). Variants can especially comprise conservative substitutions such that physiochemical characteristics of the mutated sequence are substantially identical to those of the native shorter form core+1 nucleotide sequence. Variants can also be chosen for their capacity to encode a variant shorter form core+1 protein which is recognized by antibodies directed against native shorter form core+1 protein.

Particular variants of the nucleotide sequence of FIG. 3B are derivable from amino-acid sequences of FIG. 8, including considering the variability resulting from degeneracy of the genetic code.

The invention also concerns a nucleotide sequence, such isolated DNA or RNA sequence, which hybridises under stringent conditions to a nucleotide sequence disclosed herein. Those nucleotide sequences comprise also complementary sequences of nucleotide sequences encoding a mosaic of proteins comprising core protein, shorter form core+1 protein, fragment of shorter form core+1 protein and their derivatives.

The invention also relates a nucleotide sequence which hybridises under stringent conditions with at least a complementary sequence of any nucleotide sequence disclosed above.

The invention also concerns nucleotides sequences, complementary to a sequence selected among the above disclosed sequences.

As used herein, the expression "stringent conditions" refers to conditions of severe stringency such as defined by Sambrook et al. in Molecular Cloning: a laboratory manual (1989). These conditions of high stringency are defined as following hybridisation conditions: use a prewashing solution for the nitrocellulose filters 5×SSC, 0.5% SDS, 1.0 mM EDTA (pH 8.0), hybridisation conditions of 50% formamide, 6×SSC at 42° C. and washing conditions at 68° C., 0.2×SSC and 0.1% SDS. Protocols are known to those having ordinary skill in the art. Moreover, the skilled artisan will recognize that the temperature and wash solution salt concentration can be adjust as necessary according to experimental constraints.

The invention provides a chimeric gene which comprises a promoter operatively linked to a nucleotide sequence such as described above. Promoters sequence commonly use is selected from the group consisting of lactose promoter system, tryptophan promoter system, tac promoter and CMV promoter.

As stated herein, a "chimeric gene" or "recombinant gene" consists in a DNA molecule resulting from combination or linkage of two DNA sources together, said sources not found naturally together.

The shorter form core+1 protein is "operatively linked" to a promoter such as allow a suitable transcription and translation of said shorter form core+1 sequence, said regulatory sequence is thus functionally related to the shorter form core+1 DNA sequence.

In a particular embodiment, the chimeric gene comprises a CMV/T7 chimeric promoter and a chloramphenicol acetyl transferase (CAT) gene in a first cistron and the entire internal ribosome entry site (IRES) of the HCV core coding sequence and part of the wild type core coding sequence fused to LUC gene in a second cistron. The dicistronic cassettes CAT-IRES-core-LUC were placed under the control of a CMV/T7 chimeric promoter, wherein CMV comes from Cytomegalovirus and T7 from bacteriophage, to allow the use of the same DNA plasmid for expression in vivo and in vitro. Furthermore, to eliminate the possibility of internal translation initiation events triggered by the initiator codon of the LUC gene, the ATG was changed to a GGG codon. With the above modification, the expression of the LUC gene is directly related to the expression of the fused core and coding sequences. Moreover, CAT activity serves as an internal control to standardize transfection efficiencies in vivo or potential variations in the transcript abundance in vitro.

In a preferred embodiment, the chimeric gene is constructed such as LUC gene is fused to the core sequence in a 0, +1 or −1 frames.

The open reading frame (ORF) is in frame 0, +1 or −1 such as not interrupted translation by termination codon in order to obtain a polypeptide chain, i.e. LUC polypeptide in this specific case.

It is an other object of the invention to provide a vector comprising a chimeric gene such described above. Vector according to the invention is particularly appropriate to transfer DNA sequences, e.g. chimeric gene and has properties allow protein expression.

This vector is a plasmid, a cosmid a phage or a virus. In a preferred embodiment, the vector is a plasmid selected from the group consisting of pHPI-1333 and pHPI-1335 represented in FIG. 1.

The invention also relates to recombinant cells especially mammalian cells transfected with a nucleotide sequence of the invention. By "transfection" or "transformation" it is understood the introduction of DNA into a recipient cell and its subsequent integration into said recipient cell chromosomal DNA. Methods of transfection or transformation are usual methods well known in the art, e.g. electroporation. Transfection can be either transient or stable.

Recombinant cells, which are transfected or transformed by vector, are preferably animal, mammalian or human cells. In a particular embodiment, recombinant cells are BHK-21 or Huh-1.

The invention also provides antibodies which are raised against shorter form core+1 protein or against a peptide thereof.

The invention relates to purified antibodies which specifically bind, to shorter form core+1 protein, i.e., without cross-reacting with core protein and/or core+1 protein.

As used herein, the "cross reaction" is a serological reaction in which antibodies against one antigen react with a non-identical but immunologically closely related antigen. In the present invention, antigen is the shorter form core+1 protein which has a polypeptide sequence close to core protein and/or core+1 protein.

Thus antibodies binding specifically to shorter form core+1 protein may be directed against epitopes of said protein which are not present or which are not exposed in other proteins, especially in HCV core protein or HCV core+1 protein.

The invention also concerns purified antibodies which specifically bind to polypeptide fragments common for shorter form core+1 protein, core+1 protein and optionally core protein. In a preferred embodiment, the common polypeptide fragments of the above proteins are comprised between nucleotide 897 to nucleotide 920. A preferred polypeptide fragment is illustrated above.

Monoclonal antibodies directed against the antigen of the invention can also be prepared. Methods of production monoclonal antibodies are usual methods well known in the art, including preparation of hybridoma and isolating the produced monoclonal antibodies having the required binding affinity.

Within an aspect of the invention, shorter form core+1 protein is used to prepare antibodies that specifically bind to the shorter form core+1 protein.

The invention also relates to a purified polypeptide which specifically binds to at least one purified antibody which binds itself to shorter form core+1 protein or polypeptide fragments thereof or to an antibody produced by a method using the shorter form core+1 protein or polypeptide fragments thereof as antigen. As used herein, the expression "purified polypeptide" refers to the shorter form core+1 protein of Hepatitis C virus representing at least 70%, preferably 80% or 90% of polypeptides recognized by purified antibody illustrated above.

Methods to detect an infection by Hepatitis C virus have been described below. It is possible to detect in a biological sample the infection of an individual by Hepatitis C virus by determining the presence or absence of the shorter form core+1 protein. In a preferred embodiment, the shorter form core+1 protein is detected with antibodies which are immunologicaly reactive with said protein by forming an antigen-antibody complex. Method for determining the amount of antibody bound to an antigen are well known in the art. For example, the antibody may carry a detectable marker, then a standard curve may be generated using known amounts of the tested antigen and the amount of signal generated by the marker.

The invention also relates to a method for the in vitro detection of infection by Hepatitis C virus, which consists in detecting antibodies recognizing the shorter form core+1 protein in a biological sample. The shorter form core+1 protein can be used as antigens to identify antibodies recognizing said shorter form in materials and to determine the concentration of the antibodies in those samples.

As stated herein, biological samples of an individual include but are not limited to biological fluids as urine and blood samples or tissue and cells.

In a specific embodiment, these methods employ the formation of antigen-antibody complex for the detection of HCV by means of immunoassay (direct detection) or ELISA (indirect detection). The use of immunoassay or observation of antigen-antibody by secondary reactions is well known in detecting and quantifying humoral components in fluids.

The invention also relates to immunogenic compositions, comprising HCV shorter form core+1 protein or a peptide thereof, including a specific immunogenic peptide.

Such compositions are useful to raise an immune response, either an antibody response and or preferably a CTL response in patients. Advantageously, the CTL response is such that it protects a patient against HCV infection or against its consequences. The nucleic acid sequences may also, alternatively, be involved in the preparation of immunogenic compositions.

The invention also concerns the shorter form core+1 protein for use in therapeutic compositions for the treatment of HCV infection or its consequences. Interestingly, the shorter form core+1 protein may interfere with the viral life cycle and especially down regulate HCV proliferation in patients.

The invention further relates to a method of screening compounds for their capacity to interact with viral propagation in cells infected by HCV, said method comprising:
  a) contacting said cells with a candidate compound;
  b) determining interaction between said candidate compound and expression of said shorter form core+1 protein.

The invention also concerns a method of screening compounds wherein interaction is determined by measuring the expression level of shorter form core+1 protein, prior and after contacting the HCV infected cells with a candidate compound.

Alternative translation mechanisms are used by viruses to regulate the production of structural and enzymatic proteins and, ultimately to virus propagation. Altering these translation mechanisms disrupt the virus life cycle and interact with virus production by eliminating or reducing said virus propagation. Therefore, alternative mechanisms translation provide a major target on which antiviral agents can act.

Translation mechanisms is an attractive target to identify agents that affect the efficiency of these processes. Indeed, change in initiation translation (non-ATG codon, modification of start codon) can have large effect on virus production. Furthermore, compounds that change the efficiency of translation mechanisms function at low concentrations equivalent to therapeutic concentration which do not disturb the translational machinery or cells infected by HCV virus for example.

As used herein, the term "compound" refers to inorganic or organic chemical or biological compounds either natural (isolated) or synthetic, and especially encompass nucleic acids, proteins, polypeptides, peptides, glycopeptides, lipids, lipoproteins and carbohydrates.

Blocking the translation of the core ORF has a positive effect on the translation of the level of expression of the core+1 ORF. In a preferred embodiment, the translation is two-fold increase whether the initiator ATG codon of the HCV polyprotein is converted into a stop codon. Such mutation will block core expression but also increase level of core+1 in vivo expression.

Any cells in which nucleotide sequences, chimeric genes and vectors may be transfected can be used in the screening method of the invention. In a preferred embodiment of the invention, transfected cells are animal, mammalian or human cells. In a further preferred embodiment, cells which are used in the methods of screening compounds are BHK-21 or Huh-1

The invention also concerns the compounds identified as a result of carrying out the above methods of screening.

Such compounds identified by the above methods of the invention are useful for the treatment of disorders induced by or associated with an infection by Hepatitis C virus.

These compounds, selected according to the above screening methods can be used for the preparation of a drug for the treatment or disorders induced by or associated with infection of HCV.

Some of these compounds may modulate disorders induced by or associated with infection of HCV by restoring or improving translation of the shorter form core+1 protein.

Examples of disorders resulting in HCV proliferation in host is cirrhosis, hepatocellular carcinoma or disease associated to liver chronic infection.

LEGENDS TO THE FIGURES

FIG. 1. Expression analysis of the core+1-LUC chimeric gene.

Panel A: Schematic representation of the CAT-LUC dicistronic constructs used for the tagging experiments. The entire IRES (nucleotides 9-341) and part of the core coding sequence (nucleotides 342-630) from HCV-1 and HCV-1a (H) were fused with the LUC gene under the control of both CMV and T7 promoters of pHPI-1046. The nucleotide sequences of the junction between the core and luciferase coding regions are illustrated (SEQ ID NOS: 20-22, respectively in order of appearance). The first codon of luciferase cistron, GGG, derived from the ATG initiator by site-directed mutagenesis, is boxed. The LUC gene was fused in the 0 frame relative to the preceding core coding sequence pHPI-1331 (HCV-1) and pHPI-1334 [HCV-1a (H)], in the +1 frame pHPI-1333 (HCV-1) and pHPI-1335 [HCV-1a (H)], and in the −1 frame pHPI-1332(HCV-1) and pHPI-1336 [HCV-1a (H)]. The underlined nucleotide indicates an insertion of a thymidine residue, and the inverted triangle indicates a deletion of an adenine residue.

Panels B, C: In vivo (a) and in vitro (b) expression of the HCV-1 (B) and HCV-1a (H) (C) fusion constructs.
  (a) Duplicate cultures of BHK-21 cells were transfected with each construct and the relative ratio of LUC activity to CAT quantity was determined. Bars represent the means obtained in two separate experiments in duplicate. Error bars represent the standard deviation.
  (b) Each construct was transcribed in vitro and equal amounts of all RNAs were translated in Flexi rabbit reticulocyte lysates. Translation products were directly separated by SDS-PAGE and analyzed by autoradiography. Fusion proteins are indicated by filled arrowheads. Open arrowheads show the CAT protein. NC means negative control.

FIG. 2. Effect of mutations within codons 8-11 of the HCV-1 (N 8, N19) and HCV-1a (H) (N15, N16) core coding sequence on the expression of core+1-LUC chimeric gene.

Panels A, B: The core nucleotide sequences in the region of codons 8-11 of the wildtype HCV-1 (A) (SEQ ID NO: 23) and HCV-1a (SEQ ID NO: 25) (H) (B) plasmids, as well as of the corresponding mutant variants N18, N19 (HCV-1) (A) and N15, N16 [HCV-1a (H)] (B). The wild type sequences of codons 8-11 are shown in bold. The arrows indicate the inserted mutation and the bold characters indicate the mutated nucleotides and affected amino acids. The numbers in brackets indicate the number of the mutated codons.

Panels C, D: The HCV-1 (C) and HCV-1a (H) (D) wild-type (pHPI-1333 and pHPI-1335, respectively) and corresponding mutants [pHPI-1382 (N18),-1383 (N19), and pHPI-1395 (N15),-1396 (N16), respectively] were used to transfect BHK-21 cells (a) or transcribed in vitro and equal amounts of RNAs were translated in Flexi rabbit reticulocyte lysates (b).
  (a) Duplicate cultures of BHK-21 cells were transfected with the wildtype or the mutated constructs. The activity of each mutant was calculated by determining the ratio of LUC activity to CAT quantity and is expressed as a percentage of that of the wild-type. Bars represent the means observed for three separate experiments each carried out in duplicate. Error bars correspond to the standard deviation (Peptide disclosed as SEQ ID NO:24).
  (b) 5λ of the [35S]-methionine-labeled in vitro translation products were separated by 12% SDS-PAGE and analyzed by autoradiography. The fusion protein core+1-LUC is indicated by the filled arrowhead. Open arrowheads show the CAT protein. WT and NC respectively mean wild-type and negative control (Peptide disclosed as SEQ ID NO:26).

FIG. 3. Mutational analysis of core/core+1 coding region.

Nucleotide sequence of the HCV-1 core coding region including mutations affecting the 0 (A) and +1 (B) open reading frames (ORFs). Inserted mutations are indicated by arrows. Mutated nucleotides and affected amino acids are shown in bold. Nucleotides 342 to 920 in FIG. 3B correspond to nucleotides 1-579 of SEQ ID NO:29.

Figure 4:
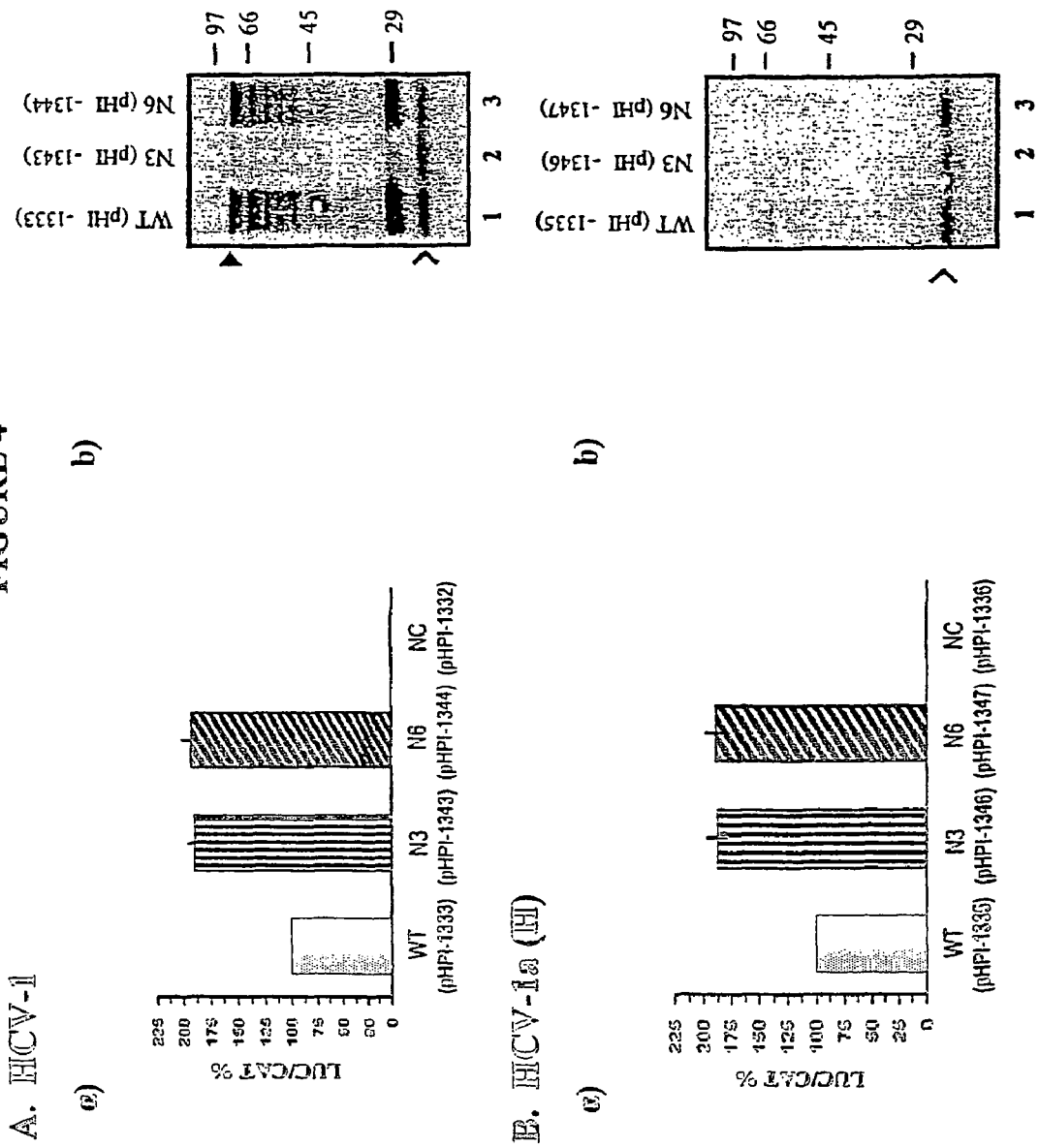

FIG. 4. Effect of mutations within nucleotide sequences that flank codons 8-11 of the HCV-1 (A) and the HCV-1a (H) (B) core coding region on the expression of core+1-LUC chimeric gene.

The wild-type pHPI-1333 (HCV-1) and pHPI-1335 [HCV-1a (H)] and N3, N6 mutant variants pHPI-1343, pHPI-1344 (HCV-1) and pHPI-1346, pHPI-1347 [HCV-1a (H)] respectively, were used to transfect BHK-21 cells (a) or transcribed in vitro and equal amounts of RNAs were translated in Flexi rabbit reticulocyte lysates (b).
  (a) Duplicate cultures of BHK-21 cells were transfected with the wild-type or the mutated constructs. The relative activity of each mutant variant was determined as described in the legend of FIG. 2. Bars represent the means from two separate experiments each performed in duplicate. Error bars indicate the standard deviation.
  (b) Translation products were resolved by SDS-PAGE and analyzed by autoradiography. Filled and open arrowheads show the chimeric core+1-LUC and CAT proteins, respectively. WT and NC respectively mean wild-type and negative control.

FIG. 5. Mutational analysis within the core+1 coding sequence of HCV-1 and HCV-1a (H) isolates.

The HCV-1 (A, C) and HCV-1a (H) (B, D) wild-type (pHPI-1333 and pHPI-1335, respectively) and mutated plasmids [pHPI-1342 (N1), -1380 (N21), -1381 (N22) and pHPI-1345 (N1), -1398 (N21), -1397 (N22), respectively] were expressed in BHK-21 (a) and Huh-7 (b) cells or in Flexi rabbit reticulocyte lysates (c).
  (a) and (b) The experiments were carried out in duplicate and repeated at least twice. The relative activity of each mutant variant was determined as described in the legend of FIG. 2. Bars represent the means. Error bars correspond to the standard deviation.
  (c) Translation products were separated by SDS-PAGE and analyzed by autoradiography. The positions of the hybrid core+1-LUC and the CAT proteins are indicated by filled and open arrowheads, respectively. WT and NC respectively mean wild-type and negative control.

FIG. 6. Effect of mutations targeting codons ATG598 and ATG604 of the core+1 coding sequence.

Duplicate cultures of BHK-21 (A) and Huh-7 (B) cells were transfected with the dicistronic HCV-1 wild-type (pHPI-1333) and mutated constructs: pHPI-1399 (N23), pHPI-1400 (N24) and pHPI-1401 (N25). The relative activity of each mutant variant was calculated as described in the legend of FIG. 2. Bars represent the means from two separate experiments each carried out in duplicate. Error bars indicate the standard deviation. WT and NC respectively mean wild-type and negative control.

Figure 7:
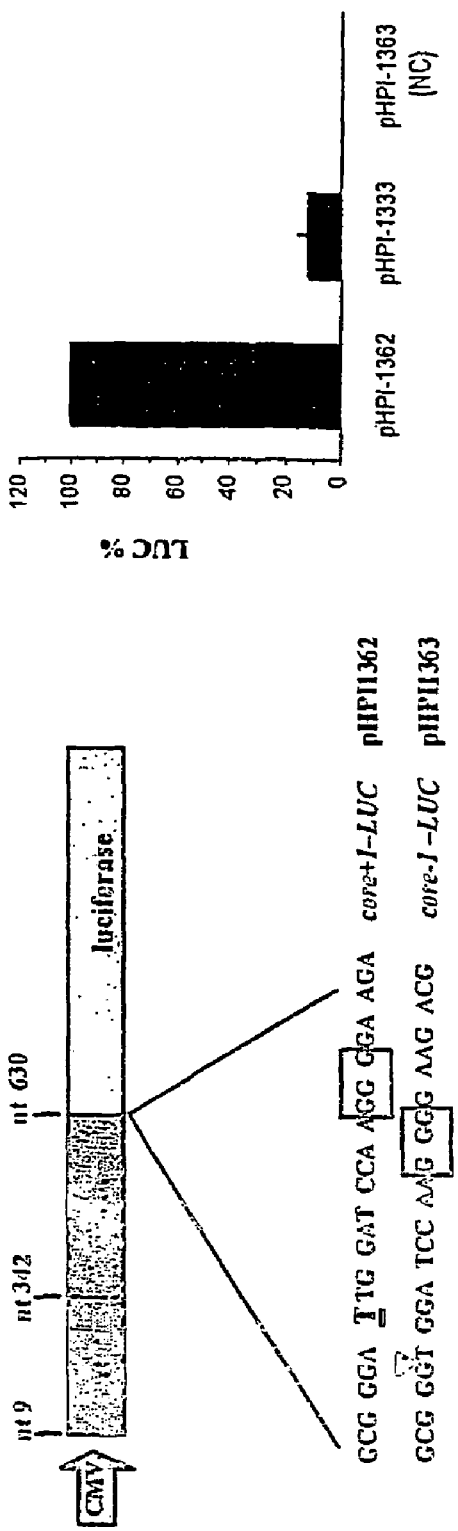
Figure 7C:
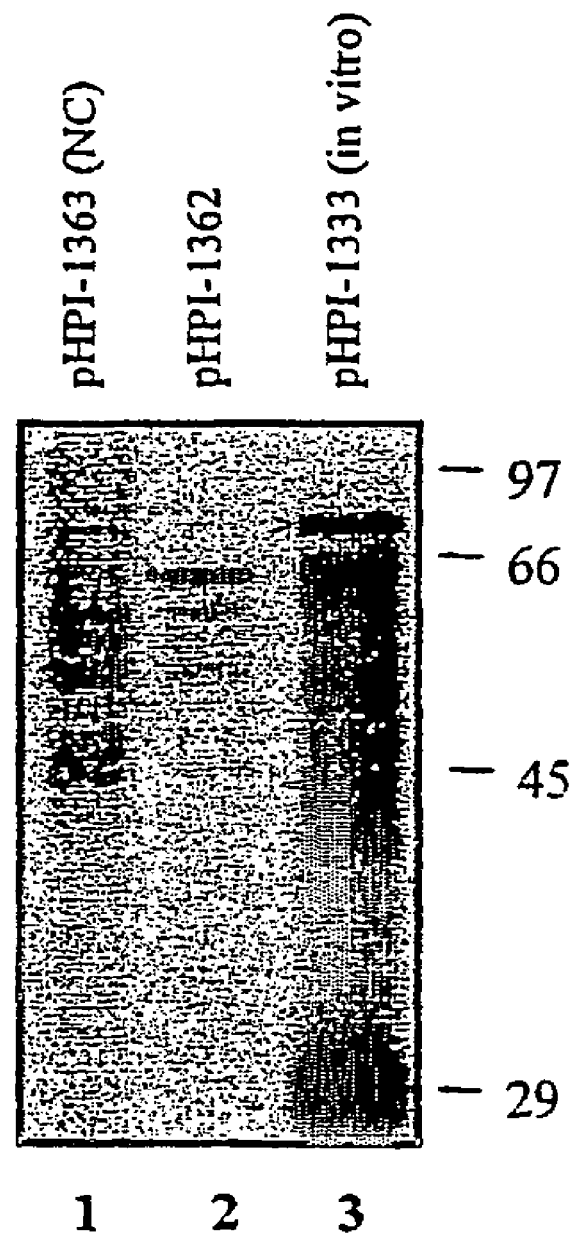

FIG. 7. Expression of the chimeric core+1-LUC protein in transfected cells.

Panel A: Schematic representation of the monocistronic constructs pHPI-1362 (core+1-LUC) (SEQ ID NO: 21) and pHPI-1363 (core-1-LUC) (SEQ ID NO: 22).

Panel B: Duplicate cultures of BHK-21 cells were transfected with the monocistronic core+1-LUC construct pHPI-1362 or the dicistronic core+1-LUC pHPI-1333 and the relative luciferase activity was determined. Bars represent the means from two separate experiments. Error bars represent the standard deviation.

Panel C: Immunoprecipitation of [35S]-methionine-labeled translation products of the core+1-LUC and core-1-LUC containing monocistronic constructs from transiently transfected BHK-21 cells using an anti-LUC goat polyclonal antibody. The immunoprecipitates were analyzed by SDS-PAGE followed by autoradiography. The hybrid core+1-LUC protein produced in vivo is marked by a dot. The open arrowhead shows the [35S]-methionine-labeled core+1-LUC protein synthesized in rabbit reticulocyte lysates. NC means negative control.

FIG. 8. Variability of the shorter form core+1 coding sequence among different variants of HCV (SEQ ID NOS: 31-50 disclosed, respectively in order of appearance).

FIG. 9. List of oligonucleotides and constructs used in the mutational analysis (SEQ ID NOS: 51-60 disclosed, respectively in order of appearance).

EXAMPLES

1. Materials and Methods 1.1 Site-Directed Mutagenesis and Plasmid Construction

Site-directed mutagenesis was carried out using the QUIKCHANGE™ kit (STRATAGENE®). The templates and oligonucleotides used in the mutational analysis and the corresponding mutants are listed in FIG. 9. All mutations were confirmed by sequence analysis.

The HCV-1 cDNA sequences thus obtained were cloned in pHPI-888 described in Varaklioti et al. 2002. The HCV-1 cDNA is obtained from pHPI-888 by PCR using sense primer, named HCVF17 (nucleotides 9-27), 5'-CGCCG-GATCCTGATGGGGGCGACACTCCAC-3' (SEQ ID NO: 14) plus antisense primer, named HCVR38 (nucleotides 342-322) 5'-CGCCGGATCCGGTGCACGGTCTACGAGACC-3' (SEQ ID NO: 15) and using sense primer, named HCVF36 (nucleotides 268-287), 5'-CGCCGGATCCGGTCGC-GAAAGGCCTTGTGG-3' (SEQ ID NO: 16) plus antisense primer, named HCVR27 (nucleotides 1052-1030), 5'-CGC-CGGATCCTCGAGGCGTTGCCCTCACGA-3' (SEQ ID NO: 17). Plasmids pHPI-888 is based on the pGEM-3zf(+) vector (PROMEGA) and contains cDNA sequence (nucleotide 9-1054) from the HCV-1 isolate (IRES-core HCV-1 sequence: accession No. M62321).

The HCV-1a (H) cDNA sequence is obtained by PCR using primers below amplifying sequence of HCV-1a (H) from pDNA-C1. The pDNA-C1 plasmid is created by insertion of the first 1064 nucleotides of HCV strain H into the vector pcDNA3) (INVITROGEN®). The cloned sequence included the 5'-NCR (nucleotides 1 to 341), the nucleocapsid coding sequence (nucleotides 342 to 914), and 150 nucleotides encoding the first 50 amino acids of the envelope E1 (nucleotides 915 to 1064) (Inchauspe et al. 1991, IRES-core HCV strain H sequence: accession number No. M67463).

The dicistronic constructs pHPI-1331, -1333 and -1332 contain the chloramphenicol acetyl transferase (CAT) gene as the first cistron followed by the entire IRES and part of the wild-type core coding sequences (nucleotides 9-630) from the prototype HCV-1 isolate fused to the firefly LUC gene in the 0, +1 and −1 frames, respectively. They were produced by site-directed mutagenesis from dicistronic pHPI-1311, -1313 and -1312, respectively, using primers 5'-TGGATC-CAAGGGGAAGACGCC-3' (SEQ ID NO: 18) (sense) and 5'-GGCGTCTTCCCCTTGGATCCA-3' (SEQ ID NO: 19) (antisense). This set of primers converts the start codon of the luciferase coding region (ATG) into a glycine codon (GGG). pHPI-1311, -1313 and -1312 were constructed by replacing the 203-bp NheI-XbaI fragment of the dicistronic pH-1046 (Psaridi et al. 1999) carrying nucleotides 249-407 of the IRES-core sequences fused with part of the LUC gene, with the 435-bp NheI-XbaI fragments of pHPI-766, -767, and -768 (Varaklioti et al. 2002), containing nucleotides 249-630 of the IRES core sequences fused with the first 50 nucleotides of the LUC gene. The dicistronic constructs pHPI-1334, -1335 and -1336 carry the entire IRES and part of the wild-type core coding region (nucleotides 9-630) from HCV-1a (H) fused to the LUC gene in all three frames (0, +1 and −1 respectively). They were derived by site-directed mutagenesis using pHPI-1328,-1329 and -1330, respectively, as templates and primers 5'-TGGATCCAAGGGGAAGACGCC-3' (SEQ ID NO: 18) (sense) and 5'-GGCGTCTTCCCCTTGGATCCA-3' (SEQ ID NO: 19) (antisense). The primers change the initiator codon of the luciferase coding region into a glycine codon (ATG→GGG). pHPI-1328,-1329 and -1330 were generated by replacing the 203-bp NheI-XbaI fragment of pHPI-1046 with the 435-bp NheI-XbaI fragments of pHPI-748,-749,-750 (Varaklioti et al. 2002), respectively. To facilitate the characterization of plasmids, most of the mutations inserted into the dicistronic constructs pHPI-1333 (HCV-1) and pHPI-1335 [HCV-1a (H)] were recloned into pHPI-1046 by replacing the wild-type 203-bp NheI-XbaI fragment with the corresponding fragment of the mutated template. The monocistronic constructs pHPI-1362 and -1363 contain the same IRES-core-LUC cassette as pHPI-1333 and -1332 respectively, cloned between the HindIII and SalI sites of pEGFPN3 (CLONTECH®).

1.2 In Vitro Translation

For all the plasmids, Flexi rabbit reticulocyte lysates (PROMEGA®) supplemented with 120 mM KCl and 0.5 mM Mg (OAc)$_2$ were used. DNA (3 μg) from each plasmid was linearized and transcribed in vitro with T7 RNA polymerase (PROMEGA®) according to the manufacturer's instructions. Wild-type pHPI-1331, -1333, -1332, -1334, -1335, -1336 and the corresponding mutated dicistronic constructs were linearized with PstI.

In vitro translation experiments were carried out on uncapped RNAs in a total volume of 25 μl using [35S]-methionine (AMERSHAM BIOSCIENCES®). The translation products (5 μl) were analyzed by 12% SDS-PAGE, transferred onto nitrocellulose membranes, and visualized by autoradiography.

1.3 Cells and DNA Transfection

BHK-21 and Huh-7 cells were maintained in Dulbecco's modified Eagle's medium (DMEM) supplemented with 10% fetal bovine serum (DMEM/FBS) at 37° C. in a 5% CO$_2$ incubator. Cells seeded in 6-well plates (60% confluence) were transfected with 1 μg plasmid DNA in the presence of LIPOFECTAMINE PLUS™ reagent (INVITROGEN®) according to the manufacturer's protocol (INVITROGEN®, Cat. No 10964-013). The medium was replaced with new DMEM/FBS 24 hours post-transfection. The cells were washed twice with phosphate buffered saline (PBS) 48 hours post-transfection and lysed in 260 μl of 1× luciferase lysis buffer (PROMEGA®). Firefly LUC was quantified by mixing 20 μl of extract with 100 μl of luciferase assay reagent (PROMEGA®) and measuring the luminescence directly with a Turner TD-20/20 luminometer. In the case of the dicistronic constructs, CAT was quantified with the CAT-ELISA kit according to the manufacturer's instructions (ROCHE®, Cat. No. 1363727).

1.4 Antibodies Production

The goat polyclonal antibody against the firefly luciferase was obtained with the kit (PROMEGA®, Cat. No. G7451) from PROMEGA® Corporation at a concentration of 1 mg/ml.

1.5 Immunopecipitation Analysis

Thirty-six hours after transfection with pHPI-1362 or pHPI-1363, monolayers of BHK-21 cells (~107 cells) were metabolically labeled for 12 hours with 20 μCi of [35S]-methionine (AMERSHAM BIOSCIENCES®) per ml methionine-free medium supplemented with 1% FBS. The labeled cells were rinsed with PBS and lysed in 500 μl total volume of triple detergent buffer consisting of 50 mM Tris (pH 8), 150 mM NaCl, 0.1% SDS, 1% Nonidet P-40, 0.5% sodium deoxycholate and 100 μg/ml phenylmethyl sulfonyl fluoride (PMSF). Cell lysates were mixed by vortexing and centrifuged at 14000×g for 10 minutes at 4° C. Clarified lysates were incubated with 10 μl of anti-LUC polyclonal antibody on a rocker overnight at 4° C. Protein G PLUSAgarose™ (SANTA CRUZ BIOTECHNOLOGY®) was added (20 μl) to this mixture and the reactions were incubated in the same conditions for an additional 2 hours. After microcentrifugation, the agarose beads were washed three times with a buffer containing 50 mM Tris (pH 8), 150 mM NaCl, 0.1% Nonidet P-40 and 1 mM EDTA. The immunoprecipitates were subsequently resolved by 10% SDS-PAGE, transferred onto nitrocellulose membranes, and detected by autoradiography.

2. Results 2.1 Core+1 ORF is Efficiently Expressed in Transfected Cells (In Vivo)

It has been previously reported that in vitro assays show detectable expression of the core+1 ORF only from the HCV-1 core coding region and not from the HCV-1a (H) isolate.

The translation of the core+1 protein from the HCV-1 and HCV-1a (H) isolates in mammalian cells has been analysed. The expression of core+1 ORF have been compared with in vitro system based on rabbit reticulocyte lysates. The cDNA sequences containing the entire IRES and part of the core coding sequences (nucleotide 9-630) from HCV-1 and HCV-1a (H) fused to the LUC gene in all three frames were transferred into a dicistronic vector in which CAT was the first gene. The dicistronic cassettes CAT-IRES-core-LUC were placed under the control of a CMV/SP6 promoter to allow the use of the same DNA plasmid for expression in vivo and in vitro. These constructs are illustrated in FIG. 1A of the present application. The expression of the LUC gene is directly related to the expression of the fused core or core+1 coding sequences, and CAT activity serves as an internal control to standardize transfection efficiencies in vivo or potential variations in the transcript abundance in vitro. Each construct was transfected into BHK-21 cells and forty-eight hours later LUC and CAT activities were measured.

In the case of HCV-1, substantial amounts of luciferase were expressed from the core+1-LUC cassette of pHPI-1333, as the levels of the luciferase activity were similar to that of the core-LUC fusion protein derived from pHPI-1331 (FIG. 1B[a]). Only background levels of luciferase activity were detected from the expression of the corresponding negative control core-1-LUC construct (pHPI-1332). Surprisingly, in contrast to in vitro, very high levels of luciferase activity were observed from construct pHPI-1335, which contains the core+1 ORF from HCV-1a (H) fused to the LUC gene. The levels were about 200% of the HCV-1a (H) core-LUC hybrid protein yielded from pHPI-1334 (FIG. 1C[a]). The corresponding negative control plasmid (pHPI-1336) resulted in background levels of luciferase expression. Thus, the HCV-1 core+1 LUC-tagged protein is efficiently produced in vivo, with similar translation levels as the core coding sequence.

These results indicate that, in contrast to expression studies in rabbit reticulocyte lysates, the HCV-1a(H), and also HCV-1, isolates efficiently express the core+1 ORF in transiently transfected BHK-21 cells.

These results also reveal differences in the translation mechanism directing the expression of core+1 ORF in vitro and in transfected cells.

2.2 A-Rich Sequence at Codons 8-11 of the Core Coding Sequence is not Essential for the Expression of the Core+1 Protein In Vivo It has been shown that the core coding region of HCV-1a (H) lacks the 10 consecutive A residues representing codons 8-11 (nucleotides 364-373) of the HCV-1 genome, which is a known slippery site for ribosomal frameshifting. The importance of the 10-A residue region on the expression of the core+1 ORF in transfected cells was also analysed and compared to that in rabbit reticulocyte lysates.

Mutational studies in 10-A residue region were also analysed in order to determine their effects on the production of the core+1 protein in vivo:

for HCV-1 (FIG. 2A), insertion of mutation N18, which contains a triple substitution of two A to G and of an A to C at nucleotides 366, 367 and 373 respectively (codons 9 and 11), gave rise to pHPI-1382, whereas mutation N19, which consists of an A to G and of two A to C change at nucleotides 367, 369 and 373 respectively (codons 9, 10 and 11), resulted in pHPI-1383;

for HCV-1a (H) (FIG. 2B), mutation N15, which consists of an A to G change at position 366 (codon 9), gave rise to pHPI-1395, and N16, which carries an A to C substitution at nucleotide 369 (codon 10), resulted in pHPI-1396. Both N15 and N16 mutations contain a single substitution as HCV-1a (H) isolate already carries a G and a C at positions 367 and 373; none of these mutations has a significant effect on luciferase activity in vivo.

This result suggests that the presence of the 10 consecutives adenines, at codons 8-11, which are only found in the HCV-1 isolate, is neither critical for core+1 expression in vivo nor for the expression of core+1 protein in rabbit reticulocyte lysates.

2.3 ATG Initiator Codon of the HCV Core Coding Sequence is not Essential for the Expression of the Core+1 Protein in Transfected Cells The molecular mechanism implicated in the in vivo expression of the core+1 ORF is further investigate according to two mutations introduced into the core coding region of the core+1-LUC-tagged constructs of both the HCV-1 and HCV-1a(H) isolates.

Mutation N3 converted the ATG initiator codon of the core ORF into a terminator codon and mutation N6 introduced a stop codon at the 25th position of the core coding sequence at nucleotide 414 (P25, CCG). The resulting plasmids were named pHPI-1343 and pHPI-1344 for HCV-1, and pHPI-1346 and pHPI-1347 for HCV-1a (H), respectively.

N3 and N6 mutations failed to block the core+1 expression in transfected cells for both HCV-1 and HCV-1a (H) isolates.

Furthermore, said N3 and N6 mutations have also increased levels of luciferase activity. On the contrary and consistent with previous in vitro studies, the N3 mutation abrogated the synthesis of the 72 kDa core+1-LUC protein from HCV-1 (FIG. 4A[b], lane 2), whereas N6 had no effect on the production of the core+1-LUC chimeric protein (FIG. 4A[b], lane 3). Furthermore, as expected according previous studies, the core+1-LUC constructs (WT, N3, N6) from HCV-1a (H) failed to produce detectable levels of the chimeric protein (FIG. 4B[b]).

These data show that differences appear between the predominant translation mechanism for core+1 expression between rabbit reticulocyte lysates (in vitro) and transfected cells (in vivo). Furthermore, these data show that the expression of core+1 ORF in vivo does not require the expression of core protein.

These results suggest that blocking the translation of the core ORF has a positive effect on the translation of the core+1 ORF and that ribosomal frameshifting is not the predominant mechanism directing core+1 expression in vivo.

2.4 Efficient Translation of the Core+1 ORF In Vivo is Mediated by Internal Initiation(s) Codon(s)

It has been shown in the above experiments that the expression of the core+1 ORF in vivo is not suppressed by changes in the initiator ATG or the A-rich region. Therefore, mutagenesis experiments have been carried out in order to test if downstream codons may function as translation initiation sites for the expression of the core+1 ORF.

To facilitate the description of the mutations affecting the core+1 ORF, the GCA alanine codon at nucleotide 346 is arbitrarily defined as the first codon of the core+1 ORF. Three nonsense mutations were separately inserted into the core+1 coding sequences of HCV-1 and HCV-1a (H):

mutation N1 introduced a TAG stop codon into the core+1 ORF at nucleotide 472 (W43, TGG), resulting in pHPI-1342 and pHPI-1345, respectively for HCV-1 and HCV-1a (H);

mutation N21 changed the 79th codon of the core+1 ORF at nucleotide 580 (G79, GGT) to a TAG stop codon, resulting in pHPI-1380 (HCV-1) and pHPI-1398 [HCV-1a (H)];

mutation N22 introduced a TAG terminator codon eight codons downstream of mutation N21 at nucleotide 604 (M87), resulting in pHPI-1381 (HCV-1) and pHPI-1397 [HCV-1a (H)].

Mutations N1 and N21 had no significant effect on the in vivo expression of the core+1-LUC gene for both HCV-1 and HCV-1a (H) isolates. On the contrary, the N22 mutation almost completely; abolished the synthesis of the core+1-LUC protein from both HCV-1 and HCV-1a (H) isolates and both BHK-21 and Huh-7 cell lines.

As expected according previous studies, mutations N1, N21 and N22 failed to support the in vitro expression of core+1 ORF.

These data show that efficient translation initiation of the core+1 ORF in transfected cells is mediated from downstream/internal initiation codons that may be located about between nucleotides 580 and 604.

The region between nucleotides 583 and 606 (codons 80-87) contains two ATG (nucleotides 598-ATGNNN ATG-606), which assess the functional importance of these ATG as initiation sites for the translation of the core+1 protein in vivo. Three following mutations have been tested:

mutation N25 converted both methionines at positions 85 and 87 to glycines, resulting in pHPI-1401;
mutation N23 altered only M85 resulting in pHPI-1399;
mutation N24 altered only M87 resulting in pHPI-1400.

The transfection of BHK-21 and Huh-7 with mutants pHPI-1399 (N23) and pHPI-1400 (N24) yielded similar levels of luciferase translation as the wild-type construct. In contrast, mutation N25 severely affected the production of the chimeric core+1-LUC protein, which was about 23% of the wildtype level in BHK-21 cells and about 26% in Huh-7.

These results suggest that the two methionines (M85 and M87) of the core+1 coding region are involved in core+1 expression since conversion of both of them to glycine significantly reduced the levels of luciferase activity.

2.5 Comparison of Size of the Core+1 Protein Produced In Vivo and In Vitro

IRES-core+1-LUC cassette contained in the dicistronic construct pHPI-1333 (HCV-1), as well as the corresponding negative control IRES-core-1-LUG cassette of pHPI-1332 were transferred into a monocistronic expression vector under the control of a CMV promoter, resulting in pHPI-1362 and pHPI-1363 respectively (FIG. 7A). This system improves the detection of the luciferase protein, as HCV IRES is more active in monocistronic constructs. Specifically, the luciferase activity exhibited by the monocistronic IRES-core+1-LUC construct pHPI-1362 in BHK-21 cells forty-eight hours post-transfection was about nine-fold higher than that yielded from the respective dicistronic pHPI-1333. Immunoprecipitation experiments were carried out with extracts of BHK-21 cells transfected with pHPI-1362, using a goat polyclonal antibody raised against luciferase.

A protein with an apparent molecular mass of around 62 kDa reacted strongly with the polyclonal antibody, this protein was clearly smaller than the chimeric protein core+1-LUC produced in vitro from the pHPI-1333 construct.

These results are consistent with above mutagenesis and show that the core+1 protein produced in mammalian cells are smaller by about 10 kDa than the core+1 protein produced in vitro.

REFERENCES

1. Choo Q L, Kuo G, Wiener A J, et al. (1989). Isolation of a cDNA clone derived from a blood-borne non-A, non-B viral hapatitis genome. Science, 244, 359-362.
2. Di Bisceglie A M. (2000) Hepathology, 31, 1014-1018.
3. Houghton M. (1996) Hepatitis C virus, Fields, ed.
4. Reed K E, and Rice C M. (2000). Curr. Top. Microbiol. Immunol. 242, 55-84.
5. Xu Z, Choi J, Yen T S, Lu W, Strohecker A, Govindarajan S, Chien D, Selby M, Ou J, (2001). Synthesis of a novel hepatitis C virus protein by ribosomal frameshift. EMBO J, 20, 3840-3848.
6. Varaklioti A, Vassilaki N, Georgopoulou U, Mavromara P. (2002) J. Biol. Chem. 277, 17713-17721.
7. U.S. Ser. No. 09/644,987 filed on Aug. 24, 2000 "Nucleic acids and new polypeptides associated with and/or overlapping with Hepatitis C virus core gene products".
8. Devereux et al. (1984). Nucl. Acids Res. 12:387.
9. Psaridi L, Georgopoulou U, Varaklioti A, Mavromara P. (1999) FEBS Lett. 453, 49-53.
10. Inchauspe G, Zebedee D H, Lee M, Sugitani M, Nasoff and A M Prince. (1991). Genomic structure of the human prototype strain H of Hepatitis C virus: comparison with American and Japanese isolates. Proc. Natl. Acad. Sci. USA 88:10292-10296.

The invention claimed is:

1. A purified shorter form core+1 protein of Hepatitis C virus (HCV), which is the product of translation of a coding sequence consisting of all or part of a nucleotide sequence extending from nucleotide 257 to nucleotide 579 of SEQ ID NO:29, within the core+1 ORF of HCV, wherein the protein comprises the epitope of SEQ ID NO: 61 or a variant thereof selected from any one of the SEQ ID NOs: 2-13.

2. The shorter form core+1 protein according to claim 1, which is encoded by a nucleotide sequence having a translation initiation codon (ATG) at nucleotide 257 or 263 of SEQ ID NO:29.

3. The shorter form core+1 protein according to claim 1, which is encoded by:
   (i) the nucleotide sequence extending from nucleotide 257 to nucleotide 487 of SEQ ID NO:29; or
   (ii) the nucleotide sequence extending from nucleotide 257 to nucleotide 556 of SEQ ID NO:29; or
   (iii) the nucleotide sequence extending from nucleotide 263 to nucleotide 487 of SEQ ID NO:29; or
   (iv) the nucleotide sequence extending from nucleotide 263 to nucleotide 556 of SEQ ID NO:29; or
   (v) the nucleotide sequence extending from nucleotide 263 to nucleotide 579 of SEQ ID NO:29.

4. The shorter form core+1 protein according to any one of claims 1 to 3, which is recognized by a serum of patients infected with HCV.

5. The shorter form core+1 protein according to claim 1, which comprises the amino-acid sequence encoded by a nucleotide sequence selected from the group consisting of nucleotides 257 to 487 of SEQ ID NO:29, nucleotides 257 to 556 of SEQ ID NO:29, and nucleotides 257 to 579 of SEQ ID NO:29.

6. The shorter form core+1 protein according to claim 1, which comprises the amino-acid sequence encoded by a nucleotide sequence selected from nucleotides 263 to 487 of SEQ ID NO:29, nucleotides 263 to 556 of SEQ ID NO:29, or nucleotides 263 to 579 of SEQ ID NO:29.

* * * * *

SEQUENCE LISTING

<160> NUMBER OF SEQ ID NOS: 65

<210> SEQ ID NO 1
<211> LENGTH: 8
<212> TYPE: PRT
<213> ORGANISM: Hepatitis C virus

<400> SEQUENCE: 1

Thr Tyr Arg Ser Ser Ala Ala Gly
 1               5

<210> SEQ ID NO 2
<211> LENGTH: 15
<212> TYPE: PRT
<213> ORGANISM: Hepatitis C virus
<220> FEATURE:
<221> NAME/KEY: MOD_RES
<222> LOCATION: (2)
<223> OTHER INFORMATION: Phe or Ser

<400> SEQUENCE: 2

Thr Xaa Arg Ser Ser Ala Pro Leu Leu Glu Ala Leu Pro Gly Pro
 1               5                  10                  15

<210> SEQ ID NO 3
<211> LENGTH: 15
<212> TYPE: PRT
<213> ORGANISM: Hepatitis C virus
<220> FEATURE:
<221> NAME/KEY: MOD_RES
<222> LOCATION: (3)
<223> OTHER INFORMATION: Leu, Pro or Arg

<400> SEQUENCE: 3

Thr Tyr Xaa Ser Ser Ala Pro Leu Leu Glu Ala Leu Pro Gly Pro
 1               5                  10                  15

<210> SEQ ID NO 4
<211> LENGTH: 15
<212> TYPE: PRT
<213> ORGANISM: Hepatitis C virus
<220> FEATURE:
<221> NAME/KEY: MOD_RES
<222> LOCATION: (5)
<223> OTHER INFORMATION: Leu

<400> SEQUENCE: 4

Thr Tyr Arg Ser Xaa Ala Pro Leu Leu Glu Ala Leu Pro Gly Pro
 1               5                  10                  15

<210> SEQ ID NO 5
<211> LENGTH: 15
<212> TYPE: PRT
<213> ORGANISM: Hepatitis C virus
<220> FEATURE:
<221> NAME/KEY: MOD_RES
<222> LOCATION: (6)
<223> OTHER INFORMATION: Val

<400> SEQUENCE: 5

Thr Tyr Arg Ser Ser Xaa Pro Leu Leu Glu Ala Leu Pro Gly Pro
 1               5                  10                  15

<210> SEQ ID NO 6
<211> LENGTH: 15
<212> TYPE: PRT

```
<213> ORGANISM: Hepatitis C virus
<220> FEATURE:
<221> NAME/KEY: MOD_RES
<222> LOCATION: (8)
<223> OTHER INFORMATION: Pro or Arg

<400> SEQUENCE: 6

Thr Tyr Arg Ser Ser Ala Pro Xaa Leu Glu Ala Leu Pro Gly Pro
 1               5                  10                  15

<210> SEQ ID NO 7
<211> LENGTH: 15
<212> TYPE: PRT
<213> ORGANISM: Hepatitis C virus
<220> FEATURE:
<221> NAME/KEY: MOD_RES
<222> LOCATION: (9)
<223> OTHER INFORMATION: Ser or Trp

<400> SEQUENCE: 7

Thr Tyr Arg Ser Ser Ala Pro Leu Xaa Glu Ala Leu Pro Gly Pro
 1               5                  10                  15

<210> SEQ ID NO 8
<211> LENGTH: 15
<212> TYPE: PRT
<213> ORGANISM: Hepatitis C virus
<220> FEATURE:
<221> NAME/KEY: MOD_RES
<222> LOCATION: (10)
<223> OTHER INFORMATION: Gly, Val, Ala or Glu

<400> SEQUENCE: 8

Thr Tyr Arg Ser Ser Ala Pro Leu Leu Xaa Ala Leu Pro Gly Pro
 1               5                  10                  15

<210> SEQ ID NO 9
<211> LENGTH: 15
<212> TYPE: PRT
<213> ORGANISM: Hepatitis C virus
<220> FEATURE:
<221> NAME/KEY: MOD_RES
<222> LOCATION: (12)
<223> OTHER INFORMATION: Ser

<400> SEQUENCE: 9

Thr Tyr Arg Ser Ser Ala Pro Leu Leu Glu Ala Xaa Pro Gly Pro
 1               5                  10                  15

<210> SEQ ID NO 10
<211> LENGTH: 15
<212> TYPE: PRT
<213> ORGANISM: Hepatitis C virus
<220> FEATURE:
<221> NAME/KEY: MOD_RES
<222> LOCATION: (13)
<223> OTHER INFORMATION: Gln

<400> SEQUENCE: 10

Thr Tyr Arg Ser Ser Ala Pro Leu Leu Glu Ala Leu Xaa Gly Pro
 1               5                  10                  15

<210> SEQ ID NO 11
<211> LENGTH: 15
<212> TYPE: PRT
<213> ORGANISM: Hepatitis C virus
<220> FEATURE:
<221> NAME/KEY: MOD_RES
<222> LOCATION: (14)
```

-continued

```
<223> OTHER INFORMATION: Glu

<400> SEQUENCE: 11

Thr Tyr Arg Ser Ser Ala Pro Leu Leu Glu Ala Leu Pro Xaa Pro
  1               5                  10                  15

<210> SEQ ID NO 12
<211> LENGTH: 15
<212> TYPE: PRT
<213> ORGANISM: Hepatitis C virus
<220> FEATURE:
<221> NAME/KEY: MOD_RES
<222> LOCATION: (15)
<223> OTHER INFORMATION: Leu or His

<400> SEQUENCE: 12

Thr Tyr Arg Ser Ser Ala Pro Leu Leu Glu Ala Leu Pro Gly Xaa
  1               5                  10                  15

<210> SEQ ID NO 13
<211> LENGTH: 16
<212> TYPE: PRT
<213> ORGANISM: Hepatitis C virus
<220> FEATURE:
<221> NAME/KEY: MOD_RES
<222> LOCATION: (16)
<223> OTHER INFORMATION: Cys, Trp or Ser

<400> SEQUENCE: 13

Thr Tyr Arg Ser Ser Ala Pro Leu Leu Glu Ala Leu Pro Gly Pro Xaa
  1               5                  10                  15

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgccggatcc tgatgggggc gacactccac                                    30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgccggatcc ggtgcacggt ctacgagacc                                    30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgccggatcc ggtcgcgaaa ggccttgtgg                                    30

<210> SEQ ID NO 17
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgccggatcc tcgaggcgtt gccctcacga                                      30

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tggatccaag gggaagacgc c                                               21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggcgtcttcc ccttggatcc a                                               21

<210> SEQ ID NO 20
<211> LENGTH: 24
<212> TYPE: DNA
<213> ORGANISM: Hepatitis C virus

<400> SEQUENCE: 20
gcgggatgga tccaagggga agac                                            24

<210> SEQ ID NO 21
<211> LENGTH: 24
<212> TYPE: DNA
<213> ORGANISM: Hepatitis C virus

<400> SEQUENCE: 21
gcgggattgg atccaagggg aaga                                            24

<210> SEQ ID NO 22
<211> LENGTH: 24
<212> TYPE: DNA
<213> ORGANISM: Hepatitis C virus

<400> SEQUENCE: 22
gcgggtggat ccaaggggaa gacg                                            24

<210> SEQ ID NO 23
<211> LENGTH: 49
<212> TYPE: DNA
<213> ORGANISM: Hepatitis C virus
<220> FEATURE:
<221> NAME/KEY: CDS
<222> LOCATION: (1)..(48)
<220> FEATURE:
<221> NAME/KEY: modified_base
<222> LOCATION: (25)..(26)
<223> OTHER INFORMATION: region may encompass the following dinucleotide
      pairs: aa, gg or ag
```

<400> SEQUENCE: 23

```
atg agc acg aat cct aaa cct caa nna maa amc aaa cgt aac acc aac c    49
Met Ser Thr Asn Pro Lys Pro Gln Xaa Xaa Xaa Lys Arg Asn Thr Asn
 1               5                  10                  15
```

<210> SEQ ID NO 24
<211> LENGTH: 16
<212> TYPE: PRT
<213> ORGANISM: Hepatitis C virus
<220> FEATURE:
<221> NAME/KEY: MOD_RES
<222> LOCATION: (9)
<223> OTHER INFORMATION: Lys, Gly, or Arg
<220> FEATURE:
<221> NAME/KEY: MOD_RES
<222> LOCATION: (10)
<223> OTHER INFORMATION: Lys or Gln
<220> FEATURE:
<221> NAME/KEY: MOD_RES
<222> LOCATION: (11)
<223> OTHER INFORMATION: Asn or Thr

<400> SEQUENCE: 24

```
Met Ser Thr Asn Pro Lys Pro Gln Xaa Xaa Xaa Lys Arg Asn Thr Asn
 1               5                  10                  15
```

<210> SEQ ID NO 25
<211> LENGTH: 49
<212> TYPE: DNA
<213> ORGANISM: Hepatitis C virus
<220> FEATURE:
<221> NAME/KEY: CDS
<222> LOCATION: (1)..(48)
<220> FEATURE:
<221> NAME/KEY: modified_base
<222> LOCATION: (25)
<223> OTHER INFORMATION: a or g
<220> FEATURE:
<221> NAME/KEY: modified_base
<222> LOCATION: (28)
<223> OTHER INFORMATION: a or c

<400> SEQUENCE: 25

```
atg agc acg aat cct aaa cct caa nga naa acc aaa cgt aac acc aac c    49
Met Ser Thr Asn Pro Lys Pro Gln Xaa Xaa Thr Lys Arg Asn Thr Asn
 1               5                  10                  15
```

<210> SEQ ID NO 26
<211> LENGTH: 16
<212> TYPE: PRT
<213> ORGANISM: Hepatitis C virus
<220> FEATURE:
<221> NAME/KEY: MOD_RES
<222> LOCATION: (9)
<223> OTHER INFORMATION: Arg or Gly
<220> FEATURE:
<221> NAME/KEY: MOD_RES
<222> LOCATION: (10)
<223> OTHER INFORMATION: Lys or Gln

<400> SEQUENCE: 26

```
Met Ser Thr Asn Pro Lys Pro Gln Xaa Xaa Thr Lys Arg Asn Thr Asn
 1               5                  10                  15
```

<210> SEQ ID NO 27
<211> LENGTH: 109
<212> TYPE: DNA
<213> ORGANISM: Hepatitis C virus
<220> FEATURE:
<221> NAME/KEY: CDS

```
<222> LOCATION: (1)..(108)
<220> FEATURE:
<221> NAME/KEY: modified_base
<222> LOCATION: (1)..(2)
<223> OTHER INFORMATION: region may encompass the following dinucleotide
      pairs: at or ta
<220> FEATURE:
<221> NAME/KEY: modified_base
<222> LOCATION: (73)..(75)
<223> OTHER INFORMATION: region may encompass either trinucleotide
      sequence: ccg or taa

<400> SEQUENCE: 27 nng agc acg aat cct aaa cct caa aaa aaa aac aaa cgt aac acc aac      48
Xaa Ser Thr Asn Pro Lys Pro Gln Lys Lys Asn Lys Arg Asn Thr Asn
 1               5                  10                  15 cgt cgc cca cag gac gtc aag ttc nnn ggt ggc ggt cag atc gtt ggt      96
Arg Arg Pro Gln Asp Val Lys Phe Xaa Gly Gly Gly Gln Ile Val Gly
             20                  25                  30 gga gtt tac ttg t                                                   109
Gly Val Tyr Leu
         35

<210> SEQ ID NO 28
<211> LENGTH: 36
<212> TYPE: PRT
<213> ORGANISM: Hepatitis C virus
<220> FEATURE:
<221> NAME/KEY: MOD_RES
<222> LOCATION: (1)
<223> OTHER INFORMATION: Met or not present
<220> FEATURE:
<221> NAME/KEY: MOD_RES
<222> LOCATION: (25)
<223> OTHER INFORMATION: Pro or not present

<400> SEQUENCE: 28

Xaa Ser Thr Asn Pro Lys Pro Gln Lys Lys Asn Lys Arg Asn Thr Asn
 1               5                  10                  15

Arg Arg Pro Gln Asp Val Lys Phe Xaa Gly Gly Gly Gln Ile Val Gly
             20                  25                  30

Gly Val Tyr Leu
         35

<210> SEQ ID NO 29
<211> LENGTH: 579
<212> TYPE: DNA
<213> ORGANISM: Hepatitis C virus
<220> FEATURE:
<221> NAME/KEY: CDS
<222> LOCATION: (5)..(484)
<220> FEATURE:
<221> NAME/KEY: CDS
<222> LOCATION: (488)..(553)
<220> FEATURE:
<221> NAME/KEY: CDS
<222> LOCATION: (557)..(577)
<220> FEATURE:
<221> NAME/KEY: modified_base
<222> LOCATION: (132)
<223> OTHER INFORMATION: a or g
<220> FEATURE:
<221> NAME/KEY: modified_base
<222> LOCATION: (239)..(241)
<223> OTHER INFORMATION: region may encompass either trinucleotide
      sequence: ggt or tag
<220> FEATURE:
<221> NAME/KEY: modified_base
<222> LOCATION: (257)..(259)
<223> OTHER INFORMATION: region may encompass either trinucleotide
      sequence: atg or ggg
```

```
<220> FEATURE:
<221> NAME/KEY: modified_base
<222> LOCATION: (263)..(265)
<223> OTHER INFORMATION: region may encompass any of the following
      trinucleotide sequences: atg, tag, or ggg

<400> SEQUENCE: 29 atga gca cga atc cta aac ctc aaa aaa aaa aca aac gta aca cca acc        49
     Ala Arg Ile Leu Asn Leu Lys Lys Lys Thr Asn Val Thr Pro Thr
     1               5                   10                  15 gtc gcc cac agg acg tca agt tcc cgg gtg gcg gtc aga tcg ttg gtg        97
Val Ala His Arg Thr Ser Ser Ser Arg Val Ala Val Arg Ser Leu Val
                20                  25                  30 gag ttt act tgt tgc cgc gca ggg gcc cta gat tng gtg tgc gcg cga       145
Glu Phe Thr Cys Cys Arg Ala Gly Ala Leu Asp Xaa Val Cys Ala Arg
             35                  40                  45 cga gaa aga ctt ccg agc ggt cgc aac ctc gag gta gac gtc agc cta       193
Arg Glu Arg Leu Pro Ser Gly Arg Asn Leu Glu Val Asp Val Ser Leu
         50                  55                  60 tcc cca agg ctc gtc ggc ccg agg gca gga cct ggg ctc agc ccg nnn       241
Ser Pro Arg Leu Val Gly Pro Arg Ala Gly Pro Gly Leu Ser Pro Xaa
     65                  70                  75 acc ctt ggc ccc tct nnn gca nnn agg gct gcg ggt ggg cgg gat ggc       289
Thr Leu Gly Pro Ser Xaa Ala Xaa Arg Ala Ala Gly Gly Arg Asp Gly
 80                  85                  90                  95 tcc tgt ctc ccc gtg gct ctc ggc cta gct ggg gcc cca cag acc ccc       337
Ser Cys Leu Pro Val Ala Leu Gly Leu Ala Gly Ala Pro Gln Thr Pro
                100                 105                 110 ggc gta ggt cgc gca att tgg gta agg tca tcg ata ccc tta cgt gcg       385
Gly Val Gly Arg Ala Ile Trp Val Arg Ser Ser Ile Pro Leu Arg Ala
            115                 120                 125 gct tcg ccg acc tca tgg ggt aca tac cgc tcg tcg gcg ccc ctc ttg       433
Ala Ser Pro Thr Ser Trp Gly Thr Tyr Arg Ser Ser Ala Pro Leu Leu
        130                 135                 140 gag gcg ctg cca ggg ccc tgg cgc atg gcg tcc ggg ttc tgg aag acg       481
Glu Ala Leu Pro Gly Pro Trp Arg Met Ala Ser Gly Phe Trp Lys Thr
    145                 150                 155 gcg tga act atg caa cag gga acc ttc ctg gtt gct ctt tct cta tct       529
Ala     Thr Met Gln Gln Gly Thr Phe Leu Val Ala Leu Ser Leu Ser
160                     165                 170 tcc ttc tgg ccc tgc tct ctt gct tga ctg tgc ccg ctt cgg cct acc       577
Ser Phe Trp Pro Cys Ser Leu Ala     Leu Cys Pro Leu Arg Pro Thr
175                 180                     185 aa                                                                     579
579

<210> SEQ ID NO 30
<211> LENGTH: 160
<212> TYPE: PRT
<213> ORGANISM: Hepatitis C virus
<220> FEATURE:
<221> NAME/KEY: MOD_RES
<222> LOCATION: (43)
<223> OTHER INFORMATION: Trp or not present
<220> FEATURE:
<221> NAME/KEY: MOD_RES
<222> LOCATION: (79)
<223> OTHER INFORMATION: Gly or not present
<220> FEATURE:
<221> NAME/KEY: MOD_RES
<222> LOCATION: (85)
<223> OTHER INFORMATION: Met or Gly
<220> FEATURE:
<221> NAME/KEY: MOD_RES
<222> LOCATION: (87)
```

<223> OTHER INFORMATION: Met, Gly or not present

<400> SEQUENCE: 30

```
Ala Arg Ile Leu Asn Leu Lys Lys Thr Asn Val Thr Pro Thr Val
1               5                   10                  15

Ala His Arg Thr Ser Ser Ser Arg Val Ala Val Arg Ser Leu Val Glu
            20                  25                  30

Phe Thr Cys Cys Arg Ala Gly Ala Leu Asp Xaa Val Cys Ala Arg Arg
        35                  40                  45

Glu Arg Leu Pro Ser Gly Arg Asn Leu Glu Val Asp Val Ser Leu Ser
    50                  55                  60

Pro Arg Leu Val Gly Pro Arg Ala Gly Pro Gly Leu Ser Pro Xaa Thr
65                  70                  75                  80

Leu Gly Pro Ser Xaa Ala Xaa Arg Ala Ala Gly Gly Arg Asp Gly Ser
                85                  90                  95

Cys Leu Pro Val Ala Leu Gly Leu Ala Gly Ala Pro Gln Thr Pro Gly
                100                 105                 110

Val Gly Arg Ala Ile Trp Val Arg Ser Ser Ile Pro Leu Arg Ala Ala
            115                 120                 125

Ser Pro Thr Ser Trp Gly Thr Tyr Arg Ser Ser Ala Pro Leu Leu Glu
    130                 135                 140

Ala Leu Pro Gly Pro Trp Arg Met Ala Ser Gly Phe Trp Lys Thr Ala
145                 150                 155                 160
```

<210> SEQ ID NO 31
<211> LENGTH: 160
<212> TYPE: PRT
<213> ORGANISM: Hepatitis C virus

<400> SEQUENCE: 31

```
Ala Arg Ile Leu Asn Leu Lys Glu Lys Pro Asn Val Thr Pro Thr Val
1               5                   10                  15

Ala His Arg Thr Ser Ser Ser Arg Val Ala Val Arg Ser Leu Val Glu
            20                  25                  30

Phe Thr Cys Cys Arg Ala Gly Ala Leu Asp Trp Val Cys Ala Arg Arg
        35                  40                  45

Gly Arg Leu Pro Ser Gly Arg Asn Leu Glu Val Asp Val Ser Leu Ser
    50                  55                  60

Pro Arg His Val Gly Pro Arg Ala Gly Pro Gly Leu Ser Pro Gly Thr
65                  70                  75                  80

Leu Gly Pro Ser Met Ala Met Arg Val Ala Gly Gly Arg Asp Gly Ser
                85                  90                  95

Cys Leu Pro Val Ala Leu Gly Leu Ala Gly Ala Pro Gln Thr Pro Gly
                100                 105                 110

Val Gly Arg Ala Ile Trp Val Arg Ser Ser Ile Pro Leu Arg Ala Ala
            115                 120                 125

Ser Pro Thr Ser Trp Gly Thr Tyr Arg Ser Ser Ala Pro Leu Leu Glu
    130                 135                 140

Ala Leu Pro Gly Pro Trp Arg Met Ala Ser Gly Phe Trp Lys Thr Ala
145                 150                 155                 160
```

<210> SEQ ID NO 32
<211> LENGTH: 142
<212> TYPE: PRT
<213> ORGANISM: Hepatitis C virus

<400> SEQUENCE: 32

-continued

```
Ala Arg Ile Leu Asn Leu Lys Glu Lys Pro Thr Val Thr Pro Thr Ala
  1               5                  10                  15

Ala His Arg Thr Ser Ser Ser Arg Ala Val Val Arg Ser Leu Val Glu
             20                  25                  30

Phe Thr Cys Cys Arg Ala Gly Ala Leu Gly Trp Val Cys Ala Arg Leu
         35                  40                  45

Gly Arg Leu Pro Ser Gly Arg Asn Leu Val Glu Gly Asp Asn Leu Ser
     50                  55                  60

Pro Arg Leu Ala Gly Pro Arg Ala Gly Pro Gly Leu Ser Pro Gly Thr
 65                  70                  75                  80

Leu Gly Pro Ser Met Ala Thr Arg Ala Trp Gly Gly Gln Asp Gly Ser
                 85                  90                  95

Cys His Pro Val Ala Pro Gly Leu Val Gly Ala Pro Gln Thr Pro Gly
            100                 105                 110

Val Ser Arg Val Ile Trp Val Arg Ser Ser Ile Pro Ser His Ala Ala
        115                 120                 125

Ser Pro Thr Ser Trp Gly Thr Phe Arg Leu Ser Ala Pro Pro
    130                 135                 140
```

<210> SEQ ID NO 33
<211> LENGTH: 124
<212> TYPE: PRT
<213> ORGANISM: Hepatitis C virus

<400> SEQUENCE: 33

```
Ala Gln Ile Leu Asn Leu Lys Glu Lys Pro Lys Glu Thr Pro Thr Val
  1               5                  10                  15

Ala His Lys Thr Leu Ser Phe Arg Ala Ala Ala Arg Ser Leu Ala Glu
             20                  25                  30

Tyr Thr Cys Cys Arg Ala Gly Ala Pro Gly Trp Val Cys Ala Arg Gln
         35                  40                  45

Gly Arg Leu Arg Ser Gly Pro Ser His Val Glu Gly Ala Ser Pro Ser
     50                  55                  60

Leu Lys Ile Gly Ala Pro Leu Ala Asn Pro Gly Glu Asn Gln Asp Thr
 65                  70                  75                  80

Pro Gly Pro Tyr Thr Gly Met Arg Asp Ser Ala Gly Gln Asp Gly Ser
                 85                  90                  95

Cys Pro Pro Glu Val Pro Val Pro Leu Gly Ala Pro Met Thr Pro Gly
            100                 105                 110

Ile Gly Arg Ala Thr Trp Val Arg Ser Ser Ile Pro
        115                 120
```

<210> SEQ ID NO 34
<211> LENGTH: 160
<212> TYPE: PRT
<213> ORGANISM: Hepatitis C virus

<400> SEQUENCE: 34

```
Ala Gln Ile Leu Asn Leu Lys Glu Lys Pro Lys Glu Thr Gln Thr Ala
  1               5                  10                  15

Ala His Arg Thr Ser Ser Ser Arg Val Ala Ala Arg Ser Leu Ala Glu
             20                  25                  30

Phe Thr Cys Cys Arg Ala Gly Ala Pro Gly Trp Val Cys Ala Arg Gln
         35                  40                  45

Gly Arg Leu Pro Ser Asp Pro Ser Arg Val Gly Asp Ala Ser Pro Ser
     50                  55                  60
```

Arg Lys Ile Gly Ala Pro Pro Ala Ser Pro Gly Glu Ser Gln Asp Ile
 65                  70                  75                  80

Leu Gly Leu Cys Met Glu Thr Arg Val Ala Val Gly Gln Val Gly Ser
             85                  90                  95

Cys Pro Leu Ala Gly Leu Val Leu Leu Gly Ala Pro Ala Thr Pro Gly
            100                 105                 110

Ile Asp His Ala Ile Trp Ala Gly Ser Ser Thr Pro Ser Arg Val Val
            115                 120                 125

Leu Pro Ile Ser Trp Gly Thr Ser Leu Ser Leu Ala Pro Leu Ser Glu
        130                 135                 140

Ala Ser Pro Glu Leu Trp His Thr Val Leu Gly Ser Trp Lys Thr Gly
145                 150                 155                 160

<210> SEQ ID NO 35
<211> LENGTH: 124
<212> TYPE: PRT
<213> ORGANISM: Hepatitis C virus

<400> SEQUENCE: 35

Ala Gln Ile Leu Asn Leu Lys Glu Lys Pro Lys Glu Thr Leu Thr Ala
 1               5                  10                  15

Ala His Arg Thr Ser Ser Ser Arg Ala Val Ala Arg Ser Leu Ala Glu
             20                  25                  30

Tyr Thr Cys Cys Arg Ala Gly Ala Arg Asp Trp Val Cys Ala Arg Arg
         35                  40                  45

Gly Lys Leu Pro Asn Gly Pro Ser His Val Gly Gly Ala Ser Pro Ser
     50                  55                  60

Leu Lys Ile Gly Ala Pro Leu Ala Ser Pro Gly Glu Gly Gln Asp Thr
 65                  70                  75                  80

Leu Gly Pro Cys Met Gly Met Arg Ala Ser Ala Gly Gln Gly Gly Ser
             85                  90                  95

Cys Pro Pro Ala Val Leu Ala Leu His Gly Ala Pro Pro Thr Pro Gly
            100                 105                 110

Ile Asn Arg Ala Thr Trp Val Arg Ser Ser Ile Pro
            115                 120

<210> SEQ ID NO 36
<211> LENGTH: 153
<212> TYPE: PRT
<213> ORGANISM: Hepatitis C virus

<400> SEQUENCE: 36

Ala Gln Ile Leu Asn Leu Lys Glu Lys Pro Lys Glu Ile Pro Thr Val
 1               5                  10                  15

Ala His Arg Thr Leu Ser Ser Arg Ala Ala Arg Ser Leu Ala Glu
             20                  25                  30

Tyr Thr Cys Cys Arg Ala Gly Ala Pro Gly Trp Val Cys Ala Arg Arg
         35                  40                  45

Gly Arg Leu Pro Asn Gly Pro Ser Arg Val Glu Gly Ala Ser Pro Ser
     50                  55                  60

Pro Lys Ile Gly Ala Thr Pro Ala Ser Pro Gly Val Ala Gln Asp Ile
 65                  70                  75                  80

Pro Gly Pro Cys Met Gly Met Arg Ala Ser Asp Gly Gln Asp Gly Ser
             85                  90                  95

Cys Pro Pro Glu Gly Pro Ala Leu His Gly Ala Pro Leu Thr Pro Gly
            100                 105                 110

```
Thr Gly Arg Val Ile Trp Val Arg Ser Ser Ile Pro Ser Pro Ala Ala
            115                 120                 125

Leu Pro Thr Ser Trp Gly Thr Ser Pro Ser Ala Pro Leu Leu Gly
    130                 135                 140

Ala Leu Pro Glu Pro Ser Arg Met Ala
145                 150

<210> SEQ ID NO 37
<211> LENGTH: 144
<212> TYPE: PRT
<213> ORGANISM: Hepatitis C virus

<400> SEQUENCE: 37

Pro Lys Glu Thr Leu Thr Ala Ala His Arg Thr Leu Ser Ser Arg Ala
1               5                   10                  15

Val Ala Arg Ser Leu Ala Glu Tyr Thr Cys Cys Arg Ala Gly Ala Pro
            20                  25                  30

Gly Trp Val Cys Ala Gln Arg Gly Arg Leu Pro Asn Gly Pro Ser His
        35                  40                  45

Val Arg Gly Ala Ser Pro Ser Pro Lys Ile Gly Ala Leu Leu Ala Ser
    50                  55                  60

Pro Gly Asp Val Gln Asp Thr Leu Gly Pro Cys Met Gly Thr Arg Ala
65                  70                  75                  80

Leu Ala Gly Gln Gly Gly Ser Cys Pro Pro Glu Ala Leu Ala Leu His
                85                  90                  95

Gly Ala Gln Pro Thr Pro Gly Thr Gly His Ala Ile Trp Val Arg Ser
            100                 105                 110

Ser Thr Pro Ser Arg Val Ala Leu Pro Thr Ser Trp Gly Thr Phe Pro
        115                 120                 125

Ser Ser Ala Pro Arg Leu Val Ala Leu Pro Glu Leu Ser His Met Val
    130                 135                 140

<210> SEQ ID NO 38
<211> LENGTH: 153
<212> TYPE: PRT
<213> ORGANISM: Hepatitis C virus

<400> SEQUENCE: 38

Ala Gln Ile Leu Asn Leu Lys Glu Lys Pro Lys Glu Thr Gln Thr Ala
1               5                   10                  15

Ala His Arg Thr Ser Ser Ser Arg Ala Val Ala Arg Ser Leu Ala Glu
            20                  25                  30

Tyr Thr Cys Cys Arg Ala Gly Ala Pro Gly Trp Val Cys Ala Arg Arg
        35                  40                  45

Gly Arg Leu Pro Asn Gly Pro Ser His Ala Glu Asp Ala Ser Pro Ser
    50                  55                  60

Pro Lys Ile Gly Val Pro Leu Ala Ser Pro Gly Asp Val Gln Asp Thr
65                  70                  75                  80

Pro Gly Pro Cys Met Gly Met Arg Ala Ser Gly Gly Gln Asp Gly Ser
                85                  90                  95

Cys Pro Pro Glu Ala Leu Ala Leu Leu Gly Ala Pro Gln Thr Pro Gly
            100                 105                 110

Ile Asp His Ala Ile Trp Ala Arg Ser Ser Ile Pro Leu Arg Val Val
        115                 120                 125

Leu Pro Ile Ser Trp Gly Thr Tyr Pro Ser Ser Ala Pro Arg Leu Ala
    130                 135                 140
```

```
Ala Leu Pro Glu His Ser Arg Met Ala
145                 150

<210> SEQ ID NO 39
<211> LENGTH: 153
<212> TYPE: PRT
<213> ORGANISM: Hepatitis C virus

<400> SEQUENCE: 39

Ala His Phe Leu Asn His Lys Glu Lys Pro Lys Glu Thr Pro Ser Val
  1               5                  10                  15

Ala His Arg Thr Leu Ser Ser Arg Val Ala Asp Arg Ser Leu Val Glu
                 20                  25                  30

Tyr Thr Cys Cys Arg Ala Gly Ala His Asp Trp Val Cys Ala Arg Arg
             35                  40                  45

Val Lys Leu Leu Asn Gly His Ser Pro Ala Asp Asp Ser Leu Ser
 50                  55                  60

Pro Arg Arg Val Arg Ala Glu Ala Gly Pro Gly Leu Ser Pro Gly Thr
 65                  70                  75                  80

Leu Gly Pro Ser Met Val Met Arg Ala Ala Gly Gln Gly Gly Ser
                 85                  90                  95

Cys Pro Arg Ala Ala Pro Val His Leu Gly Ala Gln Met Thr Pro Gly
                100                 105                 110

Gly Gly Pro Ala Ile Trp Val Lys Ser Ser Ile Pro Leu Arg Val Asp
            115                 120                 125

Ser Pro Thr Ser Trp Gly Thr Ser Arg Ser Ser Ala Pro Pro Trp Glu
        130                 135                 140

Ala Ser Gln Glu Pro Ser Arg Met Ala
145                 150

<210> SEQ ID NO 40
<211> LENGTH: 103
<212> TYPE: PRT
<213> ORGANISM: Hepatitis C virus

<400> SEQUENCE: 40

Ser Ser Arg Val Val Ala Arg Ser Leu Ala Glu Phe Thr Cys Cys Arg
  1               5                  10                  15

Ala Gly Ala Pro Gly Trp Val Cys Ala Arg Leu Glu Arg Leu Arg Ser
                 20                  25                  30

Gly Arg Asn Leu Val Ala Gly Val Asn Leu Ser Pro Arg Arg Ala Ser
             35                  40                  45

Gln Arg Ala Asp Pro Gly Arg Ser Pro Gly Thr Leu Gly Pro Ser Met
 50                  55                  60

Ala Met Arg Ala Ala Gly Gly Gln Gly Gly Ser Cys Leu Leu Ala Ala
 65                  70                  75                  80

Leu Gly His Leu Gly Ala Gln Met Ile Pro Gly Gly Asp Arg Ala Ile
                 85                  90                  95

Trp Val Arg Ser Ser Ile Pro
            100

<210> SEQ ID NO 41
<211> LENGTH: 124
<212> TYPE: PRT
<213> ORGANISM: Hepatitis C virus

<400> SEQUENCE: 41
```

Ala Arg Ile Leu Asn Leu Lys Glu Lys Pro Asn Val Thr Pro Thr Ala
1               5                   10                  15

Ala Pro Trp Thr Leu Ser Ser Arg Ala Val Ala Arg Ser Leu Ala Glu
            20                  25                  30

Phe Thr Cys Cys Arg Ala Gly Ala Pro Gly Trp Val Cys Ala Arg Leu
        35                  40                  45

Gly Arg Leu Arg Ser Gly Arg Asn Leu Val Gly Asp Val Ser Leu Ser
    50                  55                  60

Pro Arg His Val Asp Leu Arg Glu Gly Pro Gly Leu Ser Pro Gly Thr
65                  70                  75                  80

His Gly Leu Phe Thr Val Met Arg Val Ala Gly Gly Arg Asp Gly Ser
                85                  90                  95

Cys His Leu Val Ala Leu Asp Arg Leu Gly Ala Gln Met Ile Pro Gly
            100                 105                 110

Glu Gly Pro Ala Thr Trp Val Arg Ser Ser Ile Pro
        115                 120

<210> SEQ ID NO 42
<211> LENGTH: 124
<212> TYPE: PRT
<213> ORGANISM: Hepatitis C virus

<400> SEQUENCE: 42

Ala Arg Ile Leu Asn Leu Lys Glu Lys Pro Asn Val Thr Pro Thr Ala
1               5                   10                  15

Ala Gln Trp Thr Leu Ser Ser Arg Val Ala Ala Arg Ser Leu Ala Glu
            20                  25                  30

Phe Thr Cys Cys Arg Ala Gly Ala Leu Asp Trp Val Cys Ala Arg Leu
        35                  40                  45

Gly Arg Leu Arg Ser Gly Arg Asn Leu Val Gly Gly Ala Ser Leu Ser
    50                  55                  60

Pro Arg Arg Ala Asn Ser Arg Val Gly Pro Gly Leu Ser Leu Gly Ile
65                  70                  75                  80

Leu Gly Pro Phe Thr Ala Met Arg Ala Ala Gly Gly Arg Asp Gly Ser
                85                  90                  95

Cys His Pro Val Ala Leu Gly Arg Leu Gly Ala Arg Met Ile Pro Gly
            100                 105                 110

Gly Gly Pro Ala Thr Trp Val Arg Ser Ser Ile Pro
        115                 120

<210> SEQ ID NO 43
<211> LENGTH: 103
<212> TYPE: PRT
<213> ORGANISM: Hepatitis C virus

<400> SEQUENCE: 43

Asn Ser Arg Val Val Arg Ser Leu Ala Glu Phe Thr Cys Cys Arg
1               5                   10                  15

Ala Gly Ala Pro Gly Trp Val Cys Ala Arg Leu Gly Arg Leu Arg Ser
            20                  25                  30

Gly Arg Asn Leu Ala Ala Gly Val Ser Leu Ser Pro Arg His Val Gly
        35                  40                  45

Pro Arg Ala Gly Pro Gly Leu Ser Pro Gly Thr Leu Gly Leu Phe Met
    50                  55                  60

Ala Met Arg Ala Val Gly Gly Gln Gly Gly Ser Cys Pro Pro Ala Asp
65                  70                  75                  80

-continued

```
Leu Gly His Leu Gly Ala Lys Met Ile Pro Gly Val Gly Pro Ala Ile
             85                  90                  95
Trp Val Arg Ser Ser Ile Pro
            100

<210> SEQ ID NO 44
<211> LENGTH: 138
<212> TYPE: PRT
<213> ORGANISM: Hepatitis C virus

<400> SEQUENCE: 44

Ala Arg Ile Leu Asn Leu Lys Glu Lys Pro Asn Val Thr Pro Thr Val
  1               5                  10                  15

Ala Gln Trp Thr Leu Ser Ser Arg Val Val Arg Ser Leu Ala Glu
             20                  25                  30

Phe Thr Cys Cys Arg Ala Gly Ala Leu Asp Trp Val Cys Ala Arg Leu
         35                  40                  45

Gly Arg Leu Arg Ser Gly Arg Asn Leu Val Gly Ala Asn Leu Ser
     50                  55                  60

Pro Arg Arg Ala Lys Pro Arg Ala Gly Pro Gly Arg Ser Pro Gly Thr
 65                  70                  75                  80

Leu Gly Pro Phe Ser Ala Met Arg Ala Val Gly Gln Gly Gly Ser
                 85                  90                  95

Cys Pro Pro Val Ala Leu Gly Arg Pro Gly Ala Gln Met Ile Pro Gly
            100                 105                 110

Gly Gly Pro Ala Thr Trp Val Arg Ser Ser Ile Pro Ser Arg Ala Ala
        115                 120                 125

Ser Pro Thr Ser Trp Asp Thr Ser Arg Ser
    130                 135

<210> SEQ ID NO 45
<211> LENGTH: 124
<212> TYPE: PRT
<213> ORGANISM: Hepatitis C virus

<400> SEQUENCE: 45

Ala Arg Ile Leu Asn Leu Lys Glu Lys Pro Lys Glu Thr Pro Thr Ala
  1               5                  10                  15

Ala His Arg Thr Ser Ser Arg Ala Val Val Arg Ser Leu Val Glu
             20                  25                  30

Phe Thr Cys Cys Arg Ala Gly Ala Leu Gly Trp Val Cys Ala Arg Leu
         35                  40                  45

Gly Arg Leu Gln Asn Gly Arg Asn Pro Val Gly Gly Val Ser Leu Phe
     50                  55                  60

Pro Arg Arg Ala Asn Pro Arg Ala Gly Pro Gly Val Asn Pro Gly Thr
 65                  70                  75                  80

Leu Gly Pro Phe Thr Pro Met Arg Ala Ser Gly Gly Gln Gly Gly Cys
                 85                  90                  95

Ser Pro Leu Glu Ala Leu Gly Leu Thr Gly Ala Pro Met Thr Pro Gly
            100                 105                 110

Glu Asp Arg Ala Ile Trp Ala Arg Ser Ser Ile Pro
        115                 120

<210> SEQ ID NO 46
<211> LENGTH: 124
<212> TYPE: PRT
<213> ORGANISM: Hepatitis C virus
```

-continued

```
<400> SEQUENCE: 46

Ala His Phe Gln Asn Pro Lys Glu Lys Pro Lys Glu Thr Pro Pro Ala
 1               5                  10                  15

Ala Gln Trp Thr Ser Ser Arg Val Ala Val Arg Ser Leu Ala Glu
                20                  25                  30

Phe Thr Cys Cys Arg Ala Gly Ala Pro Gly Trp Val Cys Ala Arg Arg
            35                  40                  45

Glu Arg Leu Pro Ser Asp Pro Ser Pro Glu Val Gly Ala Ser Pro Tyr
        50                  55                  60

Gln Arg Arg Ala Arg Pro Arg Ala Gly Thr Gly Leu Ser Pro Asp Ile
 65                  70                  75                  80

Leu Gly Leu Phe Met Glu Thr Arg Ala Ala Gly Gly Gln Val Gly Ser
                85                  90                  95

Cys Pro Pro Ala Ala Pro Gly His Ile Gly Ala Pro Met Thr Pro Gly
            100                 105                 110

Val Asp Pro Gly Ile Trp Val Arg Ser Ser Ile Pro
        115                 120

<210> SEQ ID NO 47
<211> LENGTH: 142
<212> TYPE: PRT
<213> ORGANISM: Hepatitis C virus

<400> SEQUENCE: 47

Ala His Phe Gln Asn Pro Lys Lys Glu Thr Lys Glu Thr Gln Thr Val
 1               5                  10                  15

Ala His Arg Thr Ser Ser Arg Val Ala Val Arg Ser Leu Val Glu
                20                  25                  30

Ser Thr Cys Cys Arg Ala Gly Ala Pro Gly Trp Val Cys Ala Arg Arg
            35                  40                  45

Gly Arg Leu Leu Asn Gly Pro Ser Pro Glu Val Gly Ala Ser Pro Tyr
        50                  55                  60

Gln Arg Arg Ala Ala Arg Arg Ala Val Pro Gly His Ser Leu Gly Ile
 65                  70                  75                  80

Pro Gly Pro Ser Thr Gly Met Arg Ala Ala Ala Gly Trp Asp Gly Ser
                85                  90                  95

Cys Pro Pro Val Ala Pro Ala Arg Thr Gly Ala Leu Met Thr Pro Gly
            100                 105                 110

Glu Gly Pro Ala Thr Trp Val Lys Ser Ser Ile Pro Leu Pro Ala Ala
        115                 120                 125

Leu Pro Thr Ser Trp Gly Thr Ser Leu Ser Ser Val Pro Pro
    130                 135                 140

<210> SEQ ID NO 48
<211> LENGTH: 138
<212> TYPE: PRT
<213> ORGANISM: Hepatitis C virus

<400> SEQUENCE: 48

Ala Gln Ile Gln Asn Pro Lys Asp Lys Pro Lys Glu Thr Pro Thr Val
 1               5                  10                  15

Ala His Arg Thr Ser Ser Arg Ala Val Val Arg Ser Trp Val Glu
                20                  25                  30

Tyr Thr Cys Cys Arg Ala Gly Ala Leu Asp Trp Val Cys Ala Arg Leu
            35                  40                  45

Gly Arg Leu Pro Asn Gly Pro Ser Pro Glu Ala Gly Val Ser Pro Phe
```

```
                50                  55                  60
Gln Arg Leu Ala Ala Arg Arg Ala Val Pro Gly Val Ser Leu Gly Thr
 65                  70                  75                  80

His Gly Pro Cys Met Gly Met Arg Ala Ala Gly Gly Gln Gly Gly Ser
                 85                  90                  95

Cys Pro Pro Ala Ala Leu Ala Gln Arg Gly Ala Gln Thr Thr Pro Gly
                100                 105                 110

Val Gly Leu Ala Thr Trp Val Arg Ser Ser Ile Pro Leu Leu Ala Ala
            115                 120                 125

Ser Pro Thr Ser Trp Gly Thr Ser Pro Ser
        130                 135

<210> SEQ ID NO 49
<211> LENGTH: 127
<212> TYPE: PRT
<213> ORGANISM: Hepatitis C virus

<400> SEQUENCE: 49

Ala His Phe Gln Asn Pro Lys Glu Lys Pro Lys Glu Thr Leu Thr Val
  1               5                  10                  15

Ala Leu Trp Thr Ser Ser Arg Ala Ala Arg Ser Leu Val Glu
             20                  25                  30

Phe Thr Cys Cys Arg Ala Gly Ala Leu Val Trp Val Cys Ala Arg Arg
             35                  40                  45

Gly Arg Leu Pro Asn Gly Pro Ser Leu Glu Ala Gly Ala Ser Pro Tyr
         50                  55                  60

Gln Arg Arg Ala Ser Arg Ala Val Ala Gly Val Asn Pro Ala Thr Leu
 65                  70                  75                  80

Gly Pro Phe Met Ala Thr Arg Ala Ala Asp Gly Arg Asp Gly Ser Cys
                 85                  90                  95

Pro Pro Ala Asp Leu Gly Leu Ile Gly Ala Gln Met Thr Pro Gly Glu
                100                 105                 110

Gly Leu Ala Thr Trp Val Arg Ser Ser Ile Pro Ser Arg Ala Ala
            115                 120                 125

<210> SEQ ID NO 50
<211> LENGTH: 103
<212> TYPE: PRT
<213> ORGANISM: Hepatitis C virus

<400> SEQUENCE: 50

Ser Ser Arg Val Ala Ala Arg Ser Leu Val Glu Ser Thr Cys Tyr Arg
  1               5                  10                  15

Ala Gly Ala Leu Asp Trp Val Cys Ala Arg Arg Gly Arg Pro Pro Asn
             20                  25                  30

Gly Pro Asn Pro Glu Val Gly Val Ser Pro Tyr Gln Arg Arg Ala Ser
             35                  40                  45

Leu Arg Ala Gly Thr Gly Leu Ser Leu Val Ile Pro Gly Pro Phe Met
         50                  55                  60

Val Thr Arg Ala Ala Gly Gly Gln Gly Gly Ser Cys Leu Pro Val Ala
 65                  70                  75                  80

Leu Val Pro Thr Gly Ala Pro Met Thr Pro Gly Gly Gly His Val Thr
                 85                  90                  95

Trp Val Arg Ser Ser Ile Pro
                100
```

```
<210> SEQ ID NO 51
<211> LENGTH: 30
<212> TYPE: DNA
<213> ORGANISM: Hepatitis C virus

<400> SEQUENCE: 51
cagggrccct agattaggtg tgcgcgcgac                                30

<210> SEQ ID NO 52
<211> LENGTH: 30
<212> TYPE: DNA
<213> ORGANISM: Hepatitis C virus

<400> SEQUENCE: 52
cgtgcaccta gagcacggat cctaaacctc                                30

<210> SEQ ID NO 53
<211> LENGTH: 23
<212> TYPE: DNA
<213> ORGANISM: Hepatitis C virus

<400> SEQUENCE: 53
cgtcaagttc taaggtggcg gtc                                       23

<210> SEQ ID NO 54
<211> LENGTH: 33
<212> TYPE: DNA
<213> ORGANISM: Hepatitis C virus

<400> SEQUENCE: 54
cctaaacctc aaggaaaaac caaacgtaac acc                            33

<210> SEQ ID NO 55
<211> LENGTH: 33
<212> TYPE: DNA
<213> ORGANISM: Hepatitis C virus

<400> SEQUENCE: 55
cctaaacctc aaagacaaac caaacgtaac acc                            33

<210> SEQ ID NO 56
<211> LENGTH: 22
<212> TYPE: DNA
<213> ORGANISM: Hepatitis C virus

<400> SEQUENCE: 56
ctcagcccgt agaccttgg cc                                         22

<210> SEQ ID NO 57
<211> LENGTH: 25
<212> TYPE: DNA
<213> ORGANISM: Hepatitis C virus

<400> SEQUENCE: 57
ctctatggca tagagggctg cgggt                                     25

<210> SEQ ID NO 58
<211> LENGTH: 25
<212> TYPE: DNA
<213> ORGANISM: Hepatitis C virus

<400> SEQUENCE: 58
ttggcccctc tggggcaatg agggc                                     25
```

<210> SEQ ID NO 59
<211> LENGTH: 25
<212> TYPE: DNA
<213> ORGANISM: Hepatitis C virus

<400> SEQUENCE: 59
ctctatggca gggagggctg cgggt                                    25

<210> SEQ ID NO 60
<211> LENGTH: 32
<212> TYPE: DNA
<213> ORGANISM: Hepatitis C virus

<400> SEQUENCE: 60
ttggcccctc tggggcaggg agggctgcgg gt                            32

<210> SEQ ID NO 61
<211> LENGTH: 15
<212> TYPE: PRT
<213> ORGANISM: Hepatitis C virus

<400> SEQUENCE: 61

Thr Tyr Arg Ser Ser Ala Pro Leu Leu Glu Ala Leu Pro Gly Pro
 1               5                  10                  15

<210> SEQ ID NO 62
<211> LENGTH: 40
<212> TYPE: DNA
<213> ORGANISM: Hepatitis C virus
<220> FEATURE:
<221> NAME/KEY: CDS
<222> LOCATION: (2)..(40)

<400> SEQUENCE: 62 c ctg ctc tct tgc ttg act gtg ccc gct tcg gcc tac caa          40
  Leu Leu Ser Cys Leu Thr Val Pro Ala Ser Ala Tyr Gln
    1               5                  10

<210> SEQ ID NO 63
<211> LENGTH: 13
<212> TYPE: PRT
<213> ORGANISM: Hepatitis C virus

<400> SEQUENCE: 63

Leu Leu Ser Cys Leu Thr Val Pro Ala Ser Ala Tyr Gln
 1               5                  10

<210> SEQ ID NO 64
<211> LENGTH: 22
<212> TYPE: PRT
<213> ORGANISM: Hepatitis C virus

<400> SEQUENCE: 64

Thr Met Gln Gln Gly Thr Phe Leu Val Ala Leu Ser Leu Ser Ser Phe
 1               5                  10                  15

Trp Pro Cys Ser Leu Ala
            20

<210> SEQ ID NO 65
<211> LENGTH: 7
<212> TYPE: PRT
<213> ORGANISM: Hepatitis C virus

<400> SEQUENCE: 65

```
Leu Cys Pro Leu Arg Pro Thr
  1               5
```